United States Patent
Takahashi et al.

(10) Patent No.: US 7,206,072 B2
(45) Date of Patent: Apr. 17, 2007

(54) LIGHT SOURCE TYPE DISCRIMINATING METHOD, IMAGE FORMING METHOD, METHOD AND APPARATUS FOR ESTIMATING LIGHT SOURCE ENERGY DISTRIBUTION, AND EXPOSURE AMOUNT DETERMINING METHOD

(75) Inventors: Koji Takahashi, Kanagawa (JP); Hideyasu Ishibashi, Kanagawa (JP); Makoto Yamada, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 358 days.

(21) Appl. No.: 10/678,632

(22) Filed: Oct. 6, 2003

(65) Prior Publication Data

US 2004/0119977 A1   Jun. 24, 2004

(30) Foreign Application Priority Data

| Oct. 4, 2002 | (JP) | 2002-292032 |
| Feb. 27, 2003 | (JP) | 2003-050788 |
| Mar. 4, 2003 | (JP) | 2003-056784 |
| Mar. 14, 2003 | (JP) | 2003-070293 |

(51) Int. Cl.
    *G01N 21/25* (2006.01)
(52) U.S. Cl. .................... 356/406; 356/419
(58) Field of Classification Search ............ 356/406; 396/225; 250/226
    See application file for complete search history.

(56) References Cited

U.S. PATENT DOCUMENTS

| 4,914,738 A * | 4/1990 | Oda et al. ............... 356/226 |
| 5,298,935 A * | 3/1994 | Nagata .................. 396/225 |
| 5,636,143 A * | 6/1997 | Takahashi ............... 396/225 |
| 5,671,060 A | 9/1997 | Takahashi et al. |
| 6,201,932 B1 * | 3/2001 | Tsujimoto ............... 396/225 |
| 6,441,903 B1 * | 8/2002 | Cooper .................. 356/406 |
| 6,515,275 B1 * | 2/2003 | Hunter et al. ............ 250/226 |
| 6,822,677 B1 * | 11/2004 | Takahashi ............. 348/223.1 |
| 2003/0058350 A1 * | 3/2003 | Ishimaru et al. ....... 348/223.1 |
| 2003/0098916 A1 * | 5/2003 | Noguchi ............... 348/272 |

FOREIGN PATENT DOCUMENTS

| JP | 63-236931 | 10/1988 |
| JP | 4-310942 A | 11/1992 |
| JP | 11-177832 A | 7/1999 |
| JP | 2000-137305 A | 5/2000 |
| JP | 2001-245166 A | 9/2001 |

\* cited by examiner

*Primary Examiner*—Gregory J. Toatley, Jr.
*Assistant Examiner*—Kara Geisel
(74) *Attorney, Agent, or Firm*—Sughrue Mion, PLLC

(57) ABSTRACT

The discriminating method utilizes first to third sensors respectively having spectral sensitivities corresponding to three primary colors and a fourth sensor having a spectral sensitivity that does not overlap the spectral sensitivities corresponding to the three primary colors as sensors constituting an image pickup system, and discriminates a light source type of a photographic light source by using information obtained by the first to fourth sensors. The image forming method corrects image data of an input image using the light source type discriminated by the above light source type discriminating method.

17 Claims, 17 Drawing Sheets

◆ REFERENCE LIGHT SOURCE: CIE FLUORESCENT LAMP F8

LIGHT SOURCE TYPE
(1 TO 36: BLACK BODY COLOR TEMPERATURES,
37 TO 48: FLUORESCENT LAMPS F1 TO F12)

SIMILARITY BETWEEN LIGHT SOURCES (FLUORESCENT LAMP VS FLUORESCENT LAMP, SPECTRAL SENSITIVITY Superia 400)

SIMILARITY BETWEEN LIGHT SOURCES (FLUORESCENT LAMP VS FLUORESCENT LAMP, SPECTRAL SENSITIVITY S1pro)

— COMMERCIALLY AVAILABLE FLUORESCENT LAMP + TUNGSTEN BULB
—·— SPECTRAL WAVEFORM PREDICTED WITH PRESENT TECHNIQUE (FIRST TO THIRD MAIN COMPONENTS ARE USED)

— XENON LAMP
—·— SPECTRAL WAVEFORM PREDICTED WITH PRESENT TECHNIQUE (FIRST TO FIFTH MAIN COMPONENTS ARE USED)

LIGHT SOURCE TYPE DISCRIMINATING METHOD, IMAGE FORMING METHOD, METHOD AND APPARATUS FOR ESTIMATING LIGHT SOURCE ENERGY DISTRIBUTION, AND EXPOSURE AMOUNT DETERMINING METHOD

BACKGROUND OF THE INVENTION

1. Field of the Invention

The present invention relates to: a light source type discriminating method; an image forming method; a method and apparatus for estimating a light source energy distribution, which are adapted to determine the type of light source illuminating a subject; and an exposure amount determining method using the same. More particularly, the present invention relates to: a light source type discriminating method which makes it possible to estimate not only the color temperature of a target light source but also the type of fluorescent lamp registered in advance; an image forming method which makes it possible to estimate the type of photographic light source among various light sources including artificial light sources (12 types of fluorescent lamps defined by the CIE, for instance) and to perform appropriate image processing based on a result of this estimation; a method and apparatus for estimating a light source energy distribution, which are adapted to estimate the light source energy distribution of an illumination light source on the basis of information obtained through image pickup of a subject illuminated by the light source; and an exposure amount determining method.

2. Description of the Related Art

The printing exposure amount required when a photographic film image is printed on a duplicating sensitive material, such as photographic paper, is determined according to the quantity of light received by the photographic film (hereinafter also simply referred to as the "film") from a subject at the time of photographing, and the printing exposure amount differs from frame to frame. To obtain a print with favorable color reproductivity, it is required to correct the printing exposure amount in accordance with photographing conditions. To this end, generally, a gray balance is determined by measuring an integral transmission density for each of red (R) light, green (G) light, and blue (B) light using a photometer, which is provided with a color-separation filter formed of dye filters or vapor deposition filters, and determining an exposure amount required when a color image is reproduced on a duplicating sensitive material from an original color image for each of the R light, G light, and B light.

However, information on photographic light quality may vary depending on color failure in a background or the like, development conditions, or the like. This makes it impossible to accurately estimate the light quality, and hence the color reproductivity may become poor depending on variations in the quality of light illuminating a subject. This is because it is impossible to make a judgment as to which portions are gray on the film.

The most effective method used for detecting the gray portions on the film is to estimate the color temperature of a photographic light source.

As to this method, for instance, one of the inventors of the present invention proposes, in U.S. Pat. No. 5,636,143, a method in which the color temperature and spectral energy distribution of a photographic light source are estimated from a signal of an image recorded under given photographing conditions.

This method is aimed at estimating the color temperature of a light source used at the time of photographing a subject, and more specifically at estimating the color temperature of the light source from information on a photographed image. In brief, the principle of this method is to estimate the light source color temperature from a balance between R (red), G (green), and blue (B). For instance, G is set as a base point and the light source color temperature is estimated from a balance between R and B.

That is, information on a photographed image is a result of multiplication of the spectral energy distribution of a light source and the spectral reflectance distribution of a subject. Therefore, in this method, a process where the color temperature of the light source is assumed and the spectral reflectance of the subject is estimated based on the assumed color temperature is carried out for each of various types of light sources.

If such waveform prediction is performed on data of an image actually photographed, however, unreasonable data is obtained depending on the assumed light source. That is, there is a case where an abnormal value that is impossible under normal circumstances, such as a reflectance exceeding 100% or a negative value, is outputted.

When such an abnormal value is outputted, a process for adding the abnormal value as a penalty is performed for every pixel in an image (or certain pixels extracted from the image). FIG. 9 is an example of a graph obtained by setting the color temperature on a horizontal axis and plotting the value of the penalty described above.

In FIG. 9, it can be said that a light source having a color temperature corresponding to a point with the lowest value of the penalty has the highest possibility of being an estimation target light source that was actually used at the time of photographing.

Up to this point, we have provided an overview of the technique disclosed in U.S. Pat. No. 5,636,143, that is, a method of estimating the color temperature of a black body radiation light source by detecting reflectance abnormalities using three R, G, and B sensors.

This method makes it possible to appropriately estimate the color temperature of a black body radiation light source such as sunlight or a light source like an incandescent lamp equivalent to the sunlight. Therefore, it can be said that this method is a photographic light source estimating method that is extremely effective when a black body radiation light source is the photographic light source.

Even in this method, however, there is still a problem stemming from a fact that photo taking is performed indoors as well as outdoors. In the case of the indoor photo taking, photographs are taken under a fluorescent lamp in many cases and, as is well known, the fluorescent lamp differs from other general light sources that are black body radiation light sources. This means that it is impossible to properly estimate the type of photographic light source even by using the aforementioned method based on the color temperature detection or the method proposed by the inventor of the present invention for estimating the color temperature of a black body radiation light source.

In order to solve this problem, various techniques have been proposed up to now, although there is left unsolved the problem that when the photographic light source includes various fluorescent lamps as well as black body radiation light sources, it is impossible to sufficiently discriminate between the fluorescent lamps and the black body radiation light sources.

SUMMARY OF THE INVENTION

The present invention has been made in view of the circumstances described above, and a first object thereof is to provide a light source type discriminating method which is capable of discriminating a type of photographic light source among various light sources including fluorescent lamps, that is, a light source type.

In other words, in view of the circumstance where there is not yet found a complete method (meaning a method having at least sufficient accuracy from the viewpoint of practical use) that is applicable to a case where a photographic light source includes various fluorescent lamps and black body radiation light sources, the first object of the present invention is to modify the "color temperature estimating method, color temperature estimating apparatus, and exposure amount determining method" proposed by one of the inventors of the present invention in U.S. Pat. No. 5,636,143 described above so as to make it possible not only to estimate the color temperature of a light source, but also to discriminate among various types of light sources including at least some of artificial light sources, such as 12 types of fluorescent lamps currently defined by the CIE, which cannot be expressed by black body radiation and whose high-precision estimation has been therefore difficult according to the conventional method.

The present invention has been made in view of the circumstances described above, and a second object thereof is to provide an image forming method which is capable of estimating a type of photographic light source among various light sources including fluorescent lamps, that is, a light source type, and performing appropriate image processing based on a result of this estimation.

In other words, the second object of the present invention is to obtain the light source type discriminating method capable of discriminating the type of photographic light source among various light sources including fluorescent lamps by modifying the "color temperature estimating method, color temperature estimating apparatus, and exposure amount determining method" proposed in U.S. Pat. No. 5,636,143. Also the second object of the present invention is to make it possible to perform appropriate image processing based on a type of photographic light source discriminated according to the light source type discriminating method.

Further, a third object of the present invention is to modify the above-mentioned technique, thereby improving the estimation accuracy. More specifically, the third object of the present invention is to provide a light source energy distribution estimating method and a light source energy distribution estimating apparatus which make it possible to estimate an actual light source by estimating a spectral energy distribution of a light source used at the time of photographing including light sources whose spectral energy distributions are unknown (that is, having unknown spectral energy distributions) and whose discrimination has been therefore impossible according to the conventional technique.

A fourth object of the present invention is to provide an exposure amount determining method which makes it possible to determine an exposure amount that is optimal for effecting printing on a duplicating sensitive material based on a light source energy distribution estimated according to the light source energy distribution estimating method of the invention which attains the third object described above.

In order to attain the first object described above, a first aspect of the present invention provides a light source type discriminating method for discriminating a light source type of a photographic light source, comprising the steps of providing first to third sensors respectively having spectral sensitivities corresponding to three primary colors, arranging a fourth sensor having a spectral sensitivity that does not overlap the spectral sensitivities corresponding to the three primary colors, the first to fourth sensors constituting an image pickup system, and discriminating the light source type of the photographic light source by using information obtained by the first to fourth sensors.

Preferably the fourth sensor is a sensor in which a value of an average minimum distance $L_{min}$ indicating light source similarity between respective light sources whose types are to be discriminated is at least equal to a predetermined first reference value, the average minimum distance $L_{min}$ being represented by an expression:

$$L_{min} = \Sigma L(i) j_{min}/m \qquad (1)$$

where $L_{min}$ is the average minimum distance, $L(i)j$ is a similarity between a reference light source (i) and another light source (j) and m is a number of types of light sources, and being obtained based on differences between respective sensor signals of the reference light source (i) and respective sensor signals of another light source (j). Here, preferably, the first reference value is set at 1.2.

Preferably, the first to third sensors for the three primary colors are respectively a red (R) sensor, a green (G) sensor, and a blue (B) sensor, and the fourth sensor is a sensor having an absorption peak that exists on a longer wave side than an absorption peak of the R sensor by at least 30 nm and in a region of 700 nm or less, or the fourth sensor is a sensor whose absorption peak exists between respective absorption peaks of the G sensor and the B sensor and in a region of from 500 nm to 520 nm.

And, preferably, the light source type discriminating step using information obtained from the four sensors comprises obtaining a second reference value through one of summation and integration of products of spectral energy distributions of light sources whose color temperatures are each based on known black body radiation, spectral energy distributions of fluorescent lamps whose spectral energy distributions are prescribed, a spectral sensitivity distribution of a photometer system, and a spectral reflectance distribution expressed by a linear combination of predetermined output signal functions of the first to fourth sensors, measuring as a signal at least a part of reflection light from one of a light source whose color temperature is based on the known black body radiation and a fluorescent lamp whose type is to be discriminated, by using each of the first to fourth sensors, obtaining a spectral reflectance distribution that minimizes a difference between the second reference value and a measurement value obtained by each of the first to fourth sensors, for each light source whose color temperature is based on the known black body radiation and for each fluorescent lamp, obtaining as a first evaluation value a sum of abnormal components of the thus obtained spectral reflectance distribution whose maximum values exceed 1.0, and setting, as a result of light source type discrimination, one of a light source whose color temperature is based on the known black body radiation and a fluorescent lamp type corresponding to a minimum value of the first evaluation value.

Here, a light source type discriminating method according to the first aspect of the present invention may be effected in a structure such as a light source type discriminating apparatus implementing this method or a photographic printer having this light source type discriminating apparatus incorporated therein.

In more detail, the light source type discriminating apparatus, to which the light source type discriminating method according to the first aspect of the present invention is applied, is an apparatus that is capable of discriminating the light source type of photographic light source. In this light source type discriminating apparatus, in addition to sensors that have spectral sensitivities corresponding to three R, G, and B colors and are used for general color image analysis, a fourth sensor having the characteristics described above is arranged as a sensor constituting an image pickup system. Information obtained from these four sensors is used.

Also, a photographic printer provided with this light source type discriminating apparatus selects, for example, one of exposure correction algorithms prepared in advance with reference to the light source type discriminated by the light source type discriminating apparatus, and obtains a photographic print by performing exposure based on an exposure amount corrected using the selected exposure correction algorithm.

In order to attain the second object described above, a second aspect of the present invention provides an image forming method for reading image data of an input image with an image pickup system and performing predetermined correction on the read image data, comprising the steps of providing first to third sensors respectively having spectral sensitivities corresponding to three primary colors and arranging a fourth sensor having a spectral sensitivity that does not overlap the spectral sensitivities corresponding to the three primary colors, the first to fourth sensors constituting the image pickup system, discriminating a light source type by using information obtained by the first to fourth sensors, converting a sensor output obtained with the thus discriminated light source type, by using a color conversion method defined by the sensor output obtained with the discriminated light source type and a sensor output obtained with a desired light source type, so that a sensor output value obtained with the desired light source type is obtained, and obtaining image data of the input image read by the image pickup system using the thus obtained sensor output value.

Preferably, the first to third sensors for the three primary colors are respectively a red (R) sensor, a green (G) sensor, and a blue (B) sensor, and when the fourth sensor is assumed to be sensor X, the fourth sensor X is a sensor having an absorption peak that exists on a longer wave side than an absorption peak of the R sensor by at least 30 nm and in a region of 700 nm or less, or the fourth sensor X is a sensor whose absorption peak exists between respective absorption peaks of the G sensor and the B sensor and in a region of from 500 nm to 520 nm.

Preferably, the color conversion method comprises a step of performing correction with respect to a gray portion in the input image or a portion corresponding to the gray portion such that a sensor output $Eij^{ZE}$ (i: pixel position, j: R, G, B, X) corresponding to an estimated light source type becomes a sensor output $Eij^{ZO}$ corresponding to a reference light source.

Preferably, the correction of from the sensor output $Eij^{ZE}$ to the sensor output $Eij^{ZO}$ comprises a step of obtaining coefficient matrices A and C expressed by the following expression:

$$Ei^{ZO} = A \cdot Ei^{ZE} + C \text{ provided that} \quad (11)$$

-continued $$Ei^{ZO} = \begin{vmatrix} EiR^{ZO} \\ EiG^{ZO} \\ EiB^{ZO} \\ EiX^{ZO} \end{vmatrix}, \quad Ei^{ZE} = \begin{vmatrix} EiR^{ZE} \\ EiG^{ZE} \\ EiB^{ZE} \\ EiX^{ZE} \end{vmatrix}$$

where A and C are each a coefficient matrix and C may be zero.

Preferably, the correction of from the sensor output $Eij^{ZE}$ to the sensor output $Eij^{ZO}$ comprises a step of obtaining coefficient matrices A and C expressed by the following expression:

$$\begin{vmatrix} EiR^{ZO} \\ EiG^{ZO} \\ EiB^{ZO} \\ EiX^{ZO} \end{vmatrix} = \begin{vmatrix} AR & 0 & 0 & 0 \\ 0 & AG & 0 & 0 \\ 0 & 0 & AB & 0 \\ 0 & 0 & 0 & AX \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \quad (12)$$

where the coefficient matrix C may be zero.

Preferably, the correction of from the sensor output $Eij^{ZE}$ to the sensor output $Eij^{ZO}$ comprises a step of obtaining coefficient matrices A and C expressed by the following expression:

$$\begin{vmatrix} EiR^{ZO} \\ EiG^{ZO} \\ EiB^{ZO} \\ EiX^{ZO} \end{vmatrix} = \begin{vmatrix} AR_1 & AR_2 & AR_3 & AR_4 \\ AG_1 & AG_2 & AG_3 & AG_4 \\ AB_1 & AB_2 & AB_3 & AB_4 \\ AX_1 & AX_2 & AX_3 & AX_4 \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \quad (13)$$

where the coefficient matrix C may be zero.

Here, preferably, the light source type discriminating step using information obtained from the four R, G, B, and X sensors comprises obtaining a second reference value through one of summation and integration of products of spectral energy distributions of light sources whose color temperatures are each based on known black body radiation, spectral energy distributions of fluorescent lamps whose spectral energy distributions are prescribed, a spectral sensitivity distribution of a photometer system, and a spectral reflectance distribution expressed by a linear combination of predetermined output signal functions of the first to fourth sensors, measuring as a signal at least a part of reflection light from one of a light source whose color temperature is based on the known black body radiation and a fluorescent lamp whose type is to be discriminated, by using each of the first to fourth sensors, obtaining a spectral reflectance distribution that minimizes a difference between the second reference value and a measurement value obtained by each of the first to fourth sensors, for each light source whose color temperature is based on the known black body radiation and for each fluorescent lamp, obtaining as a first evaluation value a sum of abnormal components of the thus obtained spectral reflectance distribution whose maximum values exceed 1.0, and setting, as a result of light source type discrimination, one of a light source whose color temperature is based on the known black body radiation and a fluorescent lamp type corresponding to a minimum value of the first evaluation value.

Here, an image forming method according to the second aspect of the present invention may be effected in a structure such as a photographic printer implementing this image forming method.

In more detail, a photographic printer, to which the image forming method according to the second aspect of the present invention is applied, selects, for example, one of exposure correction algorithms prepared in advance with reference to the light source type estimated by the light source type discriminating apparatus, and obtains a photographic print by performing exposure based on an exposure amount corrected using the selected exposure correction algorithm.

In order to attain the third object described above, a third aspect of the present invention provides a light source energy distribution estimating method comprising the steps of obtaining spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions, measuring as a signal at least a part of reflection light from a light source whose spectral energy distribution is to be estimated, obtaining a spectral reflectance distribution minimizing a difference between the third reference value and a measurement value obtained by the measuring step, for each type of light source energy distribution linear combination, obtaining a sum of abnormal components of the thus obtained spectral reflectance distribution whose maximum values exceed 1.0, as a second evaluation value, and setting a light source energy distribution linear combination corresponding to a minimum value of the second evaluation value as an energy distribution of the light source whose energy distribution is to be estimated.

Preferably, the plurality of predetermined functions are each main component vectors obtained from a plurality of pieces of light source data. Further, as the main component vectors, at least first to third main components of main component vectors obtained from the plurality of pieces of light source data are preferably used, and for achieving the higher accuracy, the first to fifth components of main component vectors are more preferably used. In addition, preferably, the third reference value is obtained and stored in a storage unit in advance.

In order to attain the third object described above, a fourth aspect of the present invention provides a light source energy distribution estimating apparatus comprising storage means for storing spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions, measuring means for measuring as a signal at least a part of reflection light from a light source whose spectral energy distribution is to be estimated, spectral reflectance distribution calculating means for calculating a spectral reflectance distribution minimizing a difference between the third reference value and a measurement value obtained through measurement with the measuring means, for each type of light source energy distribution linear combination, evaluation value calculating means for calculating a sum of abnormal components of the thus obtained spectral reflectance distribution whose maximum values exceed 1.0, as a second evaluation value, and estimating means for estimating a light source energy distribution linear combination corresponding to a minimum value of the second evaluation value calculated by the evaluation value calculating means, as an energy distribution of the light source whose energy distribution is to be estimated.

Preferably, the plurality of predetermined functions are each main component vectors obtained from a plurality of pieces of light source data. Here, as the main component vectors, at least first to third main components of main component vectors obtained from the plurality of pieces of light source data are preferably used, and for achieving the higher accuracy, the first to fifth components of main component vectors are more preferably used.

Furthermore, in order to attain the fourth object described above, a fifth aspect of the present invention provides an exposure amount determining method comprising the step of determining an exposure amount for printing an image onto a duplicating sensitive material so that gray of an image to be printed of a photographic film becomes gray under an estimated light source spectral energy distribution, based on information on the estimated light source spectral energy distribution estimated with a light source energy distribution estimating method and photometric data obtained by photometrically determining at least a part of an image which is photographed on the photographic film under given photographing conditions and whose photographic light source energy distribution is to be estimated, wherein the light source energy distribution estimating method comprises the steps of obtaining spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions, measuring as a signal at least a part of reflection light from a light source whose spectral energy distribution is to be estimated, obtaining a spectral reflectance distribution minimizing a difference between the third reference value and a measurement value obtained by the measuring step, for each type of light source energy distribution linear combination, obtaining a sum of abnormal components of the thus obtained spectral reflectance distribution whose maximum values exceed 1.0, as a second evaluation value, and setting a light source energy distribution linear combination corresponding to a minimum value of the second evaluation value as an energy distribution of the light source whose energy distribution is to be estimated.

BRIEF DESCRIPTION OF THE DRAWINGS

Preferred embodiments of the present invention will be described in detail based on the following figures, wherein.

DETAILED DESCRIPTION OF THE PREFERRED EMBODIMENTS

A light source type discriminating method, an image forming method, a light source energy distribution estimating method, a light source energy distribution estimating apparatus, and an exposure amount determining method according to the present invention will now be described in detail based on preferred embodiments illustrated in the accompanying drawings.

A light source type discriminating method according to a first aspect of the present invention will be described with reference to FIGS. 1 to 15.

An embodiment to be described below of the light source type discriminating method according to the first aspect of the present invention relates to a light source type estimating method for estimating a type of light source among various light sources including fluorescent lamps using indicators showing light source similarity as reference values. In this embodiment, in addition to three sensors correspondingly provided for three primary colors that are R, G, and B, a fourth sensor (hereinafter also referred to as "X sensor" in this specification) having an absorption peak in an appropriate wavelength range is arranged. With the four R, G, B, and X sensors, the photographic light source is discriminated only using sensor signals from image pickup means (color negative film, digital still camera (DSC), or the like) without using foresight information concerning the light source and a subject.

In this embodiment, the sensor outputs are adjusted so that signal values for white having a reflectance of 1.0 becomes "$S_b = S_g = S_r = 1.0$" with respect to a black body radiation light source whose color temperature T is 5500 K. Also, the exposure amounts of the sensors are adjusted such that a G signal among the white signals with respect to an arbitrary light source becomes constant ($S_g = 1.0$).

Under the conditions described above, signal values for white numbered "19" on the Macbeth chart are obtained for 12 types of CIE fluorescent lamps (F1 to F12) and four types of black body radiation light sources (T=3000 K, 5000 K, 7000 K, and 9000 K).

Figure 1A:
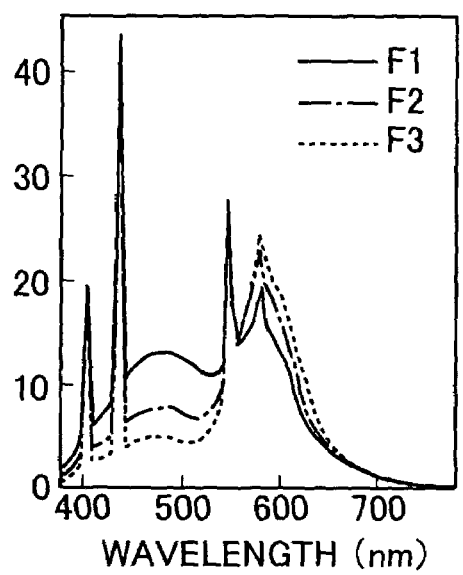
FIGS. 1A, 1B, 1C, and 1D show the schematic characteristics of 12 types of fluorescent lamps (F1 to F12) defined by the CIE.
Figure 1B:
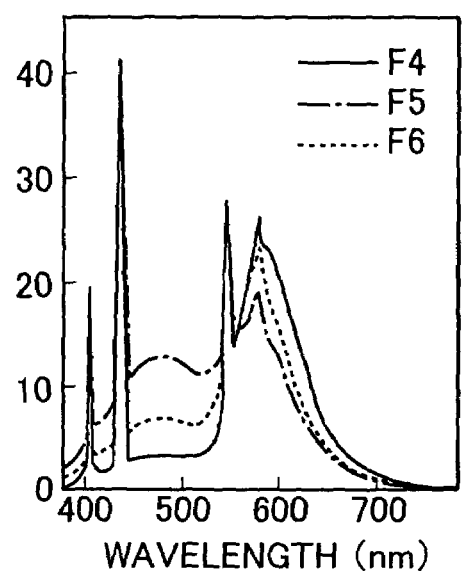
Figure 1C:
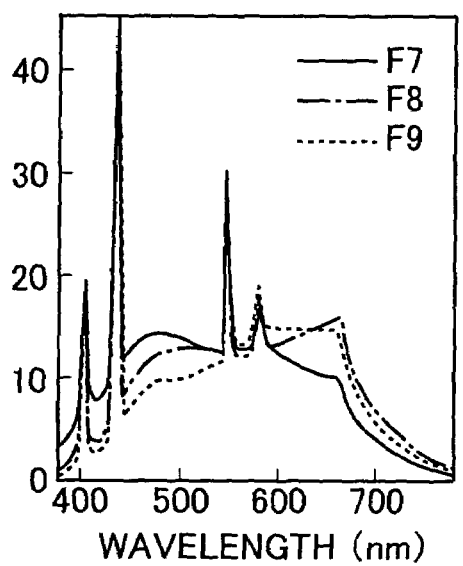
Figure 1D:
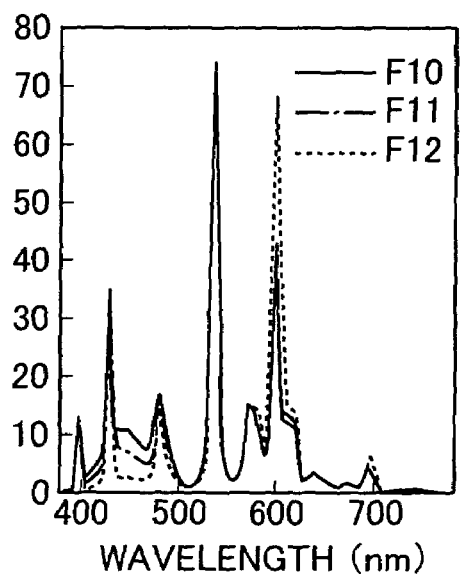
Figure 2:
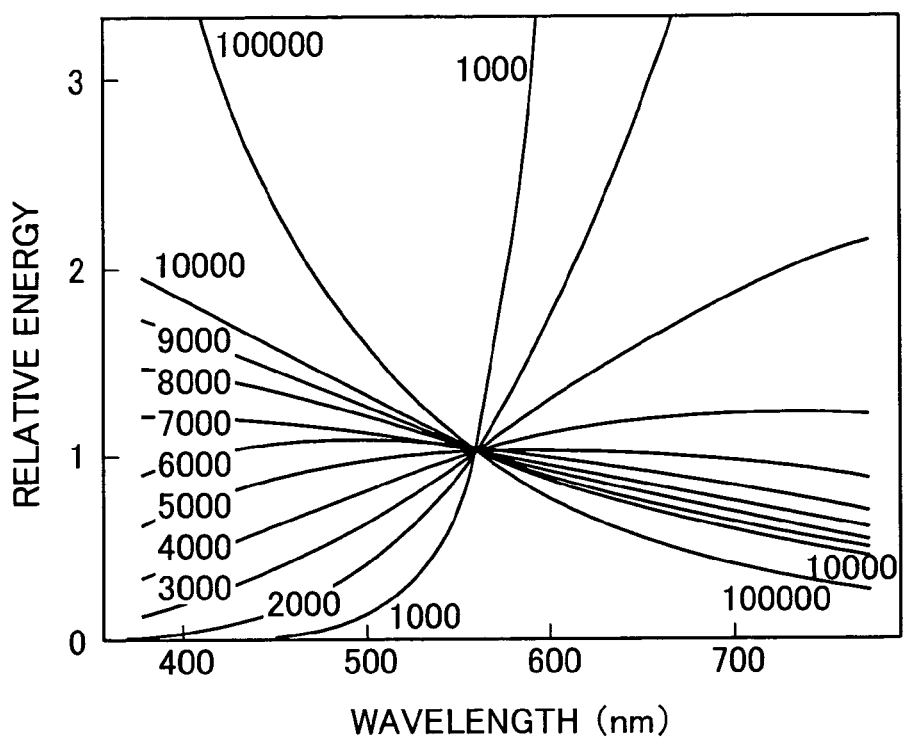
FIG. 2 illustrates a concept of black body radiation of a color temperature T.
Figure 3:
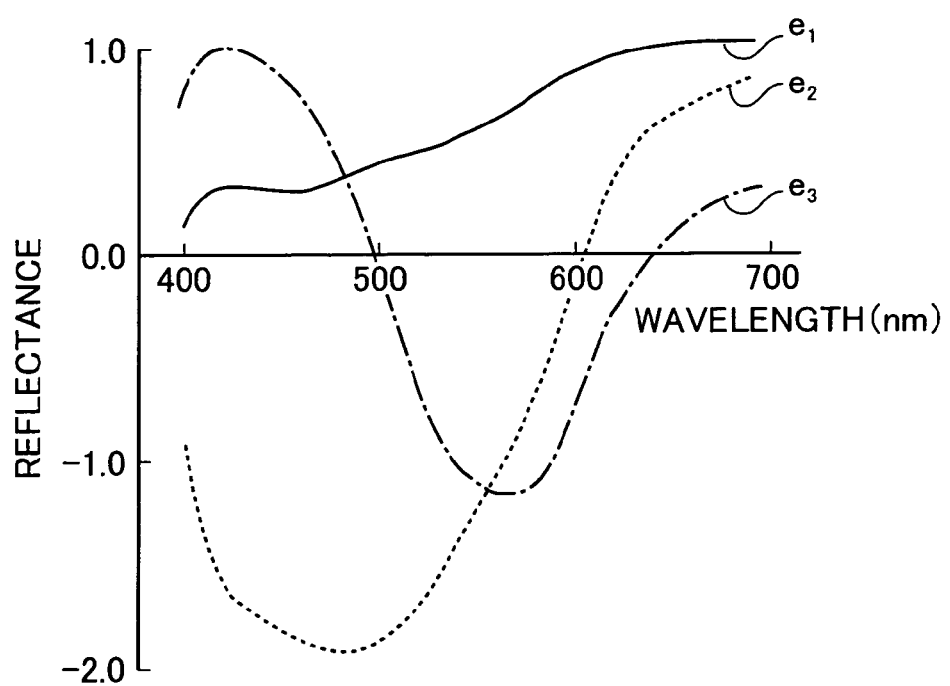
FIG. 3 shows an example of spectral distributions of eigenvectors of a subject.

Also, in this embodiment, based on these signal values, a light source color temperature is estimated and it is made possible to discriminate among various light sources including the 12 types of fluorescent lamps described above (the above-mentioned F1 to F12, under the present circumstances). FIGS. 1A to 1D each show the schematic characteristics of the aforementioned 12 types of fluorescent lamps (F1 to F12) defined by the CIE. Also, FIG. 2 shows the characteristics of the black body radiation light sources having the color temperature T. Note that it is assumed that it is possible to approximate the spectral reflectance of a subject using a weighted sum of eigenvectors (whose examples are shown in FIG. 3), as expressed by Expression (2) given below:

$$\rho_i(\lambda) = \sum_{k=1}^{4} \alpha_{ik} e_k(\lambda) \quad (2)$$

where $e_k(\lambda)$ is the eigenvector and $\alpha_{ik}(\lambda)$ is a weighting coefficient (unknown number).

As a result of this assumption, totally unexpected spectral reflectances (jagged reflectance, for instance) of the subject are excluded and therefore it becomes possible to cope only with spectral reflectances that are changed smoothly and seem to actually happen. Note that the eigenvectors shown in FIG. 3 are obtained by performing main component analysis on 24 colors of the Macbeth chart.

It is assumed that as the light source similarity indicators indicating whether the sensor signal values of light sources are close to the reference sensor signal value of a reference light source, there are used "$\Delta_b$, $\Delta_r$, $\Delta_x$" defined by Expression (3) given below:

$$\left. \begin{array}{l} \Delta_b = \log(S_b/S_b^0) \\ \Delta_r = \log(S_r/S_r^0) \\ \Delta_x = \log(S_x/S_x^0) \end{array} \right\} \quad (3)$$

where "$\Delta_b$, $\Delta_r$, $\Delta_x$" are each an indicator of a distance from the reference light source, "$S_b^0$, $S_r^0$, and $S_x^0$" are each a sensor signal of the reference light source, and "$S_b$, $S_r$, and $S_x$" are each a sensor signal of another light source.

Figure 4:
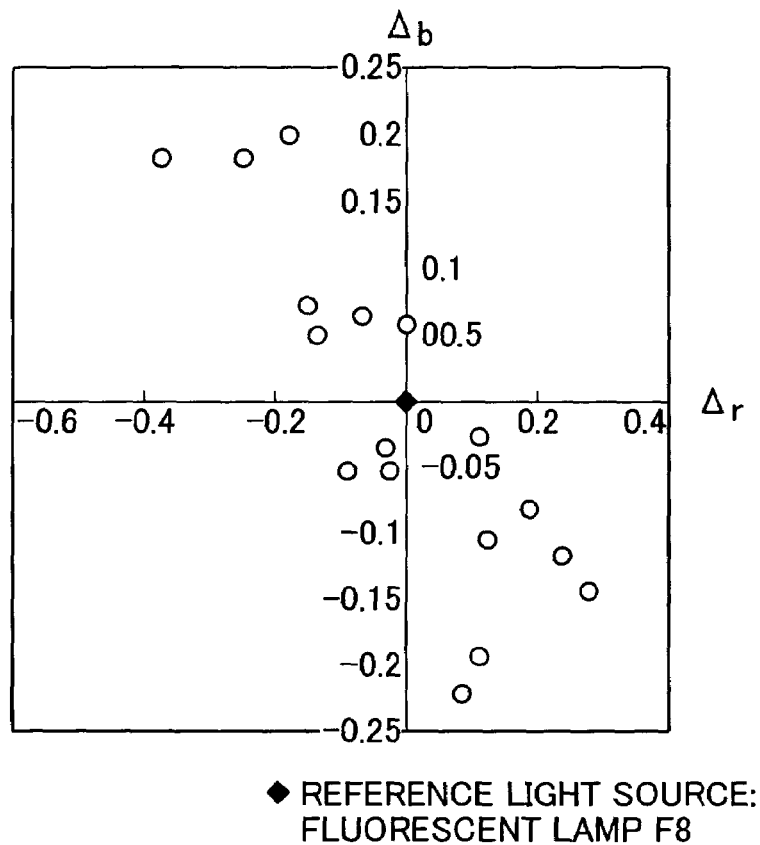
FIG. 4 is an explanatory diagram of indicators of light source similarity that are included in the principle of the present invention.

In Expression (3) described above, "$\Delta_b$, $\Delta_r$, $\Delta_x$" indicate a difference in logarithmic signal between the sensor signal of the reference light source ($S_b^0$, $S_r^0$, $S_x^0$) and the sensor signal of another light source ($S_b$, $S_r$, $S_x$). FIG. 4 shows an example of a graph where $\Delta_b$ and $\Delta_r$ are plotted by setting the CIE fluorescent lamp F8 as the reference light source (in the case of a three-signal system).

In FIG. 4, the origin is set for the reference CIE fluorescent lamp F8 and the similarity between the reference light source (F8) and other light sources is reduced in accordance with an increase in distance from the origin.

In the case of a four-signal system, there is added a component "$\Delta_x$" in a direction perpendicular to the paper plane of FIG. 4. In the four-signal system, it is possible to evaluate the similarity between the reference light source (F8) and other light sources with reference to a distance L to the origin in a three-dimensional space, as expressed by Expression (4) given below:

$$L = \sqrt{(\Delta_b^2 + \Delta_r^2 + \Delta_x^2)} \quad (4)$$

where L is the distance between the reference light source and another light source and "$\Delta_b$, $\Delta_r$, $\Delta_x$" are each an indicator of a distance from the reference light source.

"L" in Expression (4) is rewritten as "L(i)j" by giving additional letters thereto and it is assumed that L(i)j indicates a distance from the reference light source (i) to another light source (j). For instance, if the reference light source and other light sources are both CIE fluorescent lamps (12 types), this results in a situation where 11 L(i)j exist for each reference light source. Therefore, the minimum value among 11 L(i)j is set as $L(i)_{min}$ and $L_{min}$ is calculated using Expression (5) given below:

$$L_{min} = \Sigma L(i)_{min}/12 (i=F1 \sim F12) \quad (5)$$

where $L_{min}$ is an average minimum distance and $L(i)_{min}$ is the minimum value of L(i)j.

Here, $L_{min}$ is an average minimum distance among the 12 types of CIE fluorescent lamps, so that as this value is reduced, the similarity between the fluorescent lamps is increased and the probability of occurrence of misidentifications is increased.

Figure 5:
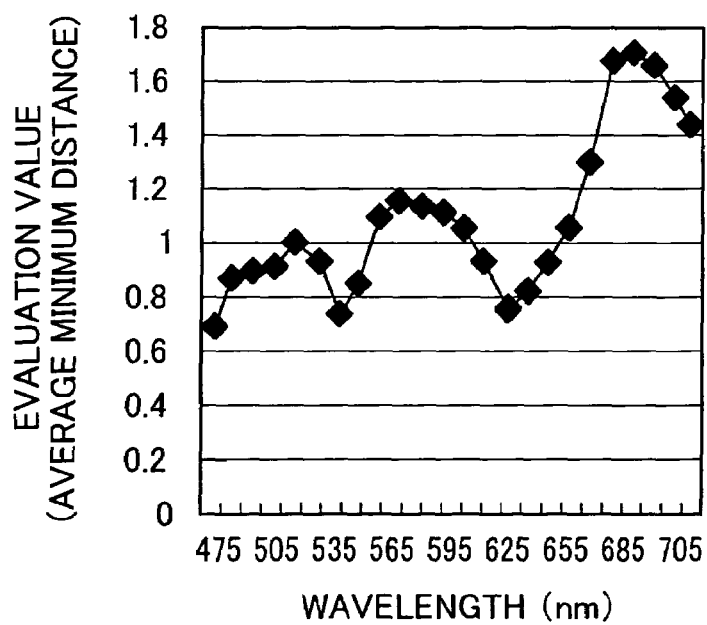
FIG. 5 is an explanatory diagram showing how an average minimum distance between fluorescent lamps moves when a peak position (wavelength) of a spectral sensitivity of an X sensor according to an embodiment of the present invention is changed.

FIG. 5 shows how the average minimum distance $L_{min}$ between the aforementioned 12 types of CIE fluorescent lamps moves when the peak position (waveform) of the spectral sensitivity of the X sensor (fourth sensor) described above is changed. As can be seen from FIG. 5, $L_{min}$ described above becomes maximum when the peak waveform of the X sensor is set in the vicinity of 675 nm. That is, in order to prevent the misidentifications among the CIE fluorescent lamps (12 types) as reliably as possible, it is preferable that the peak waveform of the fourth sensor is set at around 675 nm.

Figure 6:
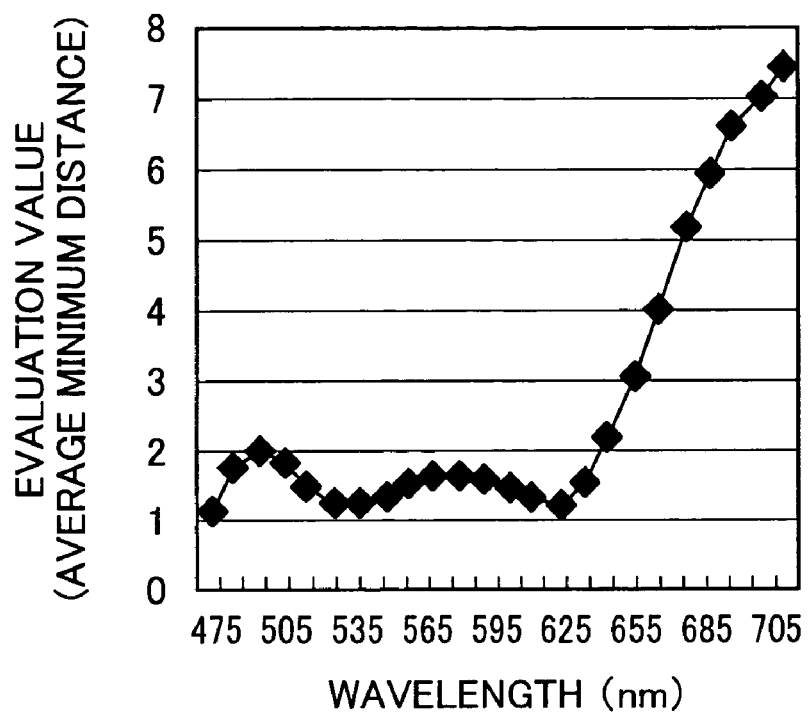
FIG. 6 is an explanatory diagram showing how the similarity changes when the peak position (wavelength) of the spectral sensitivity of the X sensor is changed under a state where the fluorescent lamps and black body radiation light sources are included.

Also, as to the similarity between the fluorescent lamps and the black body radiation light sources, a result of investigation conducted according to a similar method is shown in FIG. 6. According to the results shown in FIG. 6, it is understood that as the peak position of the spectral sensitivity of the fourth sensor is set on a longer wavelength side, the average minimum distance $L_{min}$ is increased and therefore the probability of occurrence of misidentifications between the fluorescent lamps and the black body radiation light sources is reduced.

From the results described above, it can be said that it is optimum that the peak position of the spectral sensitivity of the fourth sensor is set in the vicinity of 680 nm.

Figure 7:
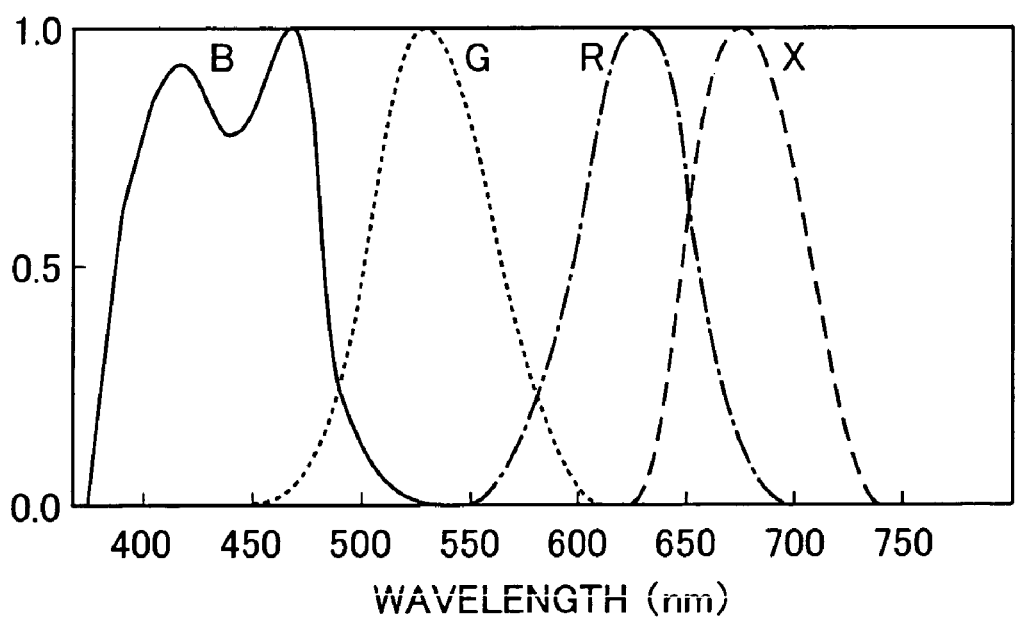
FIG. 7 shows an example of the spectral sensitivity of each of R, G, B, and X (X1, X2) sensors used in the embodiment.

In FIG. 7, the spectral sensitivity characteristics of each sensor in this case are summarized.

EXAMPLE 1

The type of photographic light source is estimated through image simulation under conditions where sensor spectral sensitivities are set in a manner shown in FIG. 7 and spectral reflectance data is obtained from a multi-spectrum image (1024×1024 pixels).

As light source data, images are created for 16 types of light sources consisting of 12 types of CIE fluorescent lamps and 4 types of black body radiation light sources (each of which has already been described above) with respect to one set of sensor spectral sensitivity pairs. At this time, three sensor spectral sensitivity pairs are obtained for a three-signal system, a four-signal system (peak wavelength of the X sensor is set at 645 nm: X1), and a four-signal system (peak wavelength of the X sensor is set at 675 nm: X2), and are compared with each other.

Also, the light source estimating method (program) disclosed in U.S. Pat. No. 5,636,143 described above is applied to the three-signal system and the four-signal systems.

In brief, according to the light source estimating method (program) described above, the spectral reflectance of each pixel in an input image is reproduced by assuming that the image is created under a certain light source (assumed light source). If the assumed light source differs from a light source (actual light source) that was actually used at the time of photographing, an abnormality (reflectance exceeding 1.0) is observed in the spectral reflectance. By utilizing this phenomenon, a light source having the minimum reflectance abnormality is estimated as the actual light source.

A more concrete description will be given below.

In the following description, it is assumed that in addition to the three sensors provided for the three primary colors that are R, G, and B (three-signal system), a sensor having an absorption peak of 645 nm (first four-signal system) or an absorption peak of 680 nm (second four-signal system) is provided as the fourth sensor, and these sensors are used.

Generally, when a subject illuminated by a black body radiation light source having a certain color temperature or a certain type of fluorescent lamp is photographed, a sensor output signal $E_{ij}^Z$ ("Z" indicates a black body radiation light source having the color temperature T or a certain type of fluorescent lamp) can be expressed by Expression (6) given below:

$$E_{ij}^Z = \int P^Z(\lambda)\rho_i(\lambda)S_j(\lambda)d\lambda \quad (j=B, G, R, X) \tag{6}$$

where $E_{ij}^Z$ is the sensor output signal, $P^Z(\lambda)$ is the spectral energy distribution of the light source, $\rho_i(\lambda)$ is the spectral reflectance distribution of the subject, and $S_j(\lambda)$ is the spectral sensitivity distribution of the sensor (known).

Here, the sensor signal $E_{ij}^Z$ described above is an integral value containing two unknown variables $P^Z(\lambda)$ and $\rho_i(\lambda)$, and many combinations of $P^Z(\lambda)$ and $\rho_i(\lambda)$ giving the sensor signal $E_{ij}^Z$ are conceivable. Accordingly, it is generally impossible to specify the light source $P^Z(\lambda)$, although it is conceivable that the possible combinations contain many combinations in which mathematical contradictions do not arise but physical contradictions arise. Therefore, by eliminating such combinations with physical contradictions, it becomes possible to perform the light source estimation within certain accuracy.

It should be noted here that "i" of $\rho_i(\lambda)$ in Expression (6) representing the spectral reflectance distribution of the subject is determined by the format of information used to obtain the data. That is, in the case of a photographed image obtained by photographing a subject, information can be obtained from each of pixels obtained by dividing the photographed image into many portions. Hence, $\rho_i(\lambda)$ represents the spectral reflectance distribution of the part of the subject that corresponds to an i-th pixel.

When Expression (2) described above is substituted into Expression (6) and $P^Z(\lambda)$ is rewritten as $P(T;\lambda)$, the sensor signal $E_{ij}^Z$ is expressed by Expression (7) given below:

$$E_{ij}^Z = \int P(T;\lambda)S_j(\lambda)\sum_{k=1}^{4}\alpha_{ik}e_k(\lambda)d\lambda \quad (j=B, G, R, X) \tag{7}$$

where $P(T;\lambda)$ is the spectral energy distribution of a light source having the color temperature T.

In this example, under these conditions, in order to obtain possible combinations of the light source and the subject, the spectral reflectance of the subject is restored while fixing the color temperature T that is one of unknown numbers. For that purpose, an initial value is given to a weighting coefficient $\alpha_{ik}$, and calculation for optimizing the weighting coefficient $\alpha_{ik}$ is repeated until the integral value on the right side of Expression (7) coincides with the sensor signal $E_{ij}^Z$. Then, the spectral reflectance of the subject is restored from Expression (2) using the converged weighting coefficient $\alpha_{ik}$.

Figure 8:
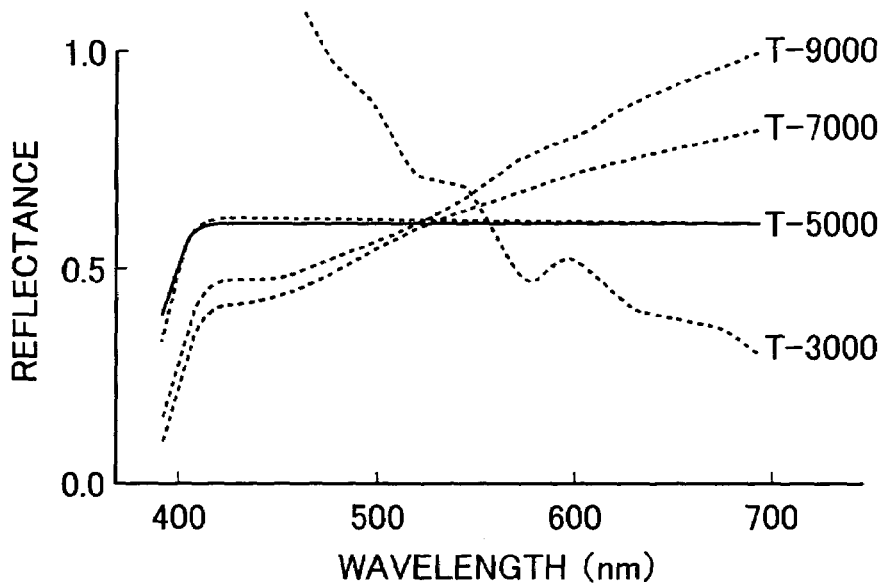
FIG. 8 shows an example of a state where a spectral reflectance of a subject is restored.

An example of the above is shown in FIG. 8. In this example, the sensor signal $E_{ij}^Z$ is set as "$E_B=E_G=E_R=E_X=0.6$", and the color temperature T is changed from 3000 K, through 5000 K and 7000 K, to 9000 K. Here, when T is set at 3000 K and 9000 K (long wavelength side), a part of the spectral reflectance exceeds a reflectance of 1.0 and becomes the aforementioned physically contradictory data (reflectance abnormality). Consequently, it can be said that the possibility of the color temperature of the photographic light source being 3000 K or 9000 K is low.

As described above, it is conceivable that the restored data of the spectral reflectance is applicable to the color temperature estimation. In addition, several evaluation values contributing to the estimation are also conceivable. As described above, the spectral reflectance $\rho_i(\lambda)$ falls within the range of $0 \leq \rho_i(\lambda) \leq 1.0$, so that it is conceivable that the more the spectral reflectance $\rho_i(\lambda)$ exceeds 1.0, the more the spectral reflectance $\rho_i(\lambda)$ deviates from the "true color temperature". Therefore, in this example, an evaluation value v as expressed by Expression (8) given below is introduced as one evaluation value:

$$v = \rho_i(\lambda)^{max} - 1.0 \tag{8}$$

where v is set at 0 when $v \leq 0$.

This evaluation value v becomes a function of the color temperature T, and a value obtained by totalizing the evaluation values v concerning many pixels (i=1, ..., u) is set as V. Here, V is expressed by Expression (9) given below:

$$V = \sum_{i=1}^{n} v = \sum_{i=1}^{n}(\rho_i(\lambda)^{max} - 1.0) \tag{9}$$

$\rho_i(\lambda)^{max}$ is the maximum value of $\rho_i(\lambda)$.

Figure 9:
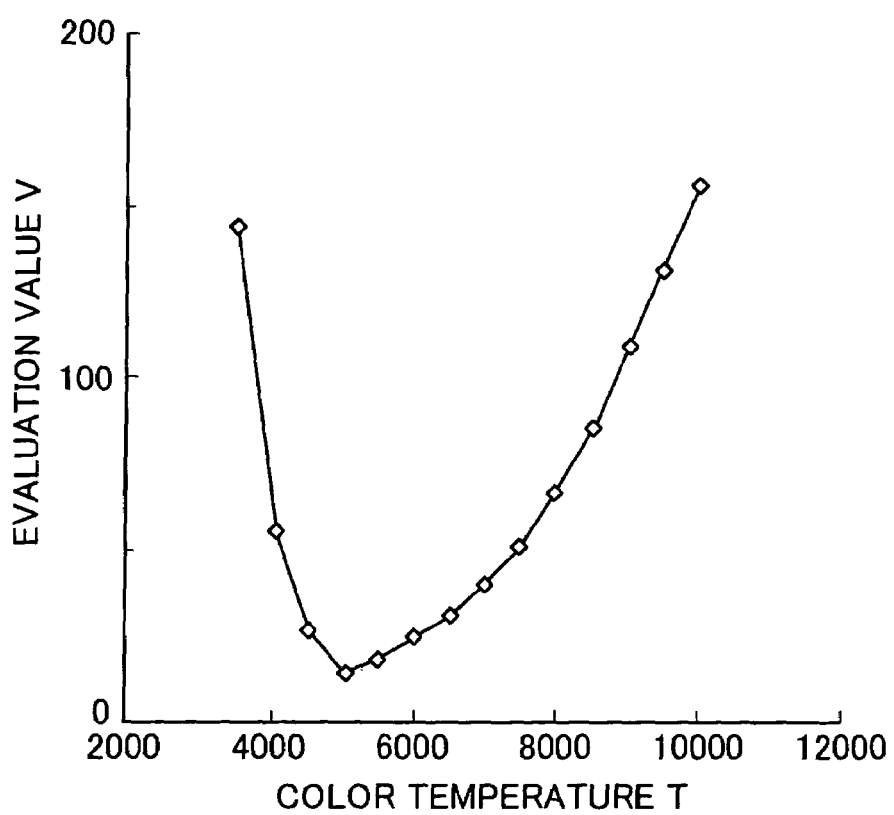
FIG. 9 shows an example of a relationship between the color temperature T and an evaluation value V according to an embodiment of the present invention.

FIG. 9 schematically shows how the evaluation value V varies when the color temperature described above is changed. In FIG. 9, there is shown a case where the light source type is a black body radiation light source whose color temperature is 5000 K, and it can be said that the part corresponding to the bottom of the U-letter shaped curve in FIG. 9 is where the possibility of the spectral reflectance of the subject exceeding the reflectance of 1.0 is minimum as described above. Therefore, it is possible to estimate (discriminate) that the color temperature corresponding to this part is the color temperature of the photographic light source.

Figure 10:
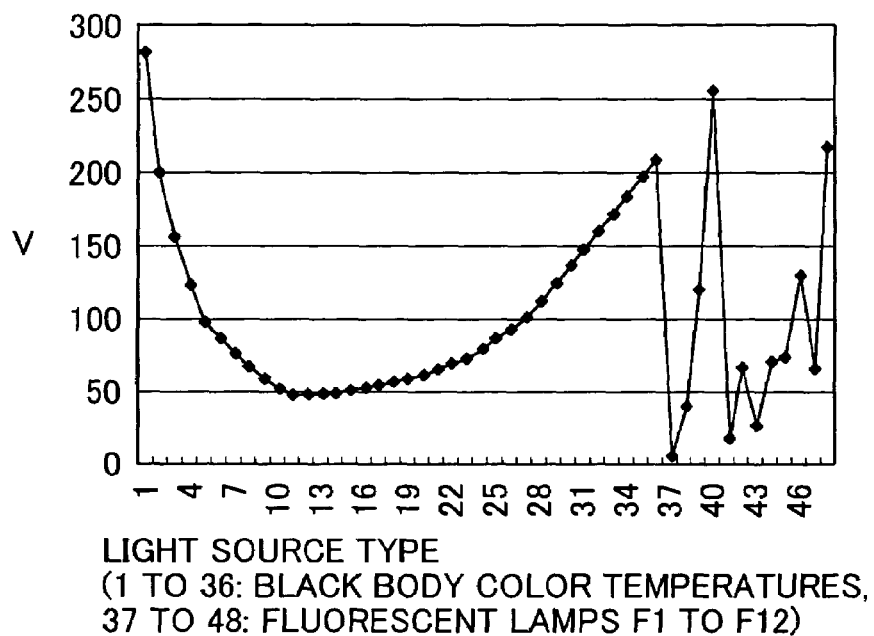
FIG. 10 shows an example of a relationship between (i) the color temperature T and the 12 types of fluorescent lamps and (ii) the evaluation value V according to the embodiment.

FIG. 10 shows a case where the type of the photographic light source is the fluorescent lamp F1. When discrimination among various light sources including the fluorescent lamps is to be performed, the evaluation value V in Expression (9) described above is calculated for each color temperature of the black body radiation light source and each of the 12 types of fluorescent lamp light sources. Then, the type of the black body radiation light source or the fluorescent lamp whose color temperature corresponding to the minimum value of the U-letter or V-letter shaped curve is known is estimated as the light source type of the photographic light source. In FIG. 10, it can be read that the light source type corresponding to the minimum value is the fluorescent lamp F1.

Figure 11:
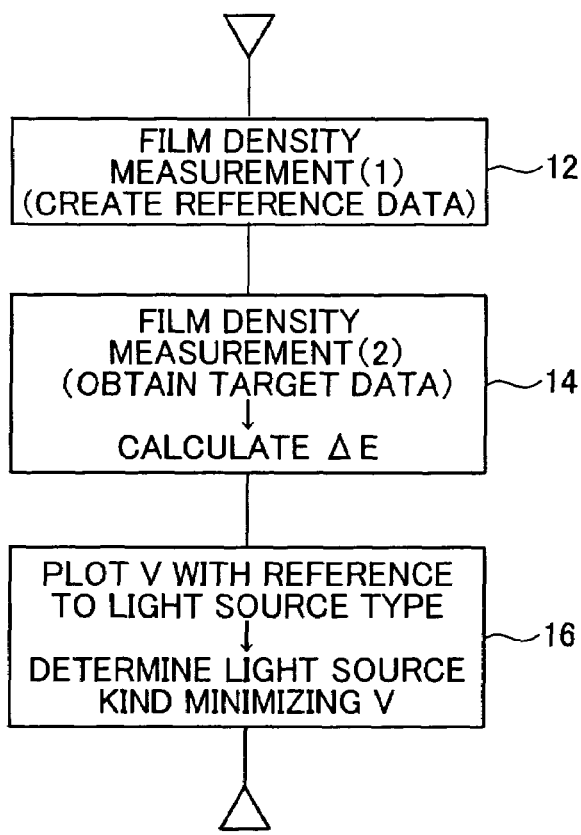
FIG. 11 is a flowchart showing the flow of a light source type discriminating operation according to the embodiment.

FIG. 11 is a flowchart showing the flow of an operation performed in this example to discriminate the type of the photographic light source. Note that in the following description, there will be described, as an example, a case where a color negative film is subjected to photometry (density measurement) and the type of the photographic light source is discriminated based on the result of the photometry.

In step 12, as advance preparations, various light source types (including the fluorescent lamps described above) are assumed, the spectral reflectance of a measurement target color negative film is restored by giving arbitrary four numerical value pairs to the weighting coefficient $\alpha_{ik}$ (Expression (2)), $E_{ij}^Z$ is calculated using Expression (6), and the calculation result is accumulated in a memory. By repeating this operation, data pairs of $\alpha_{ik}$ and $E_{ij}^Z$ are constructed. Results of this calculation may be converted into a table.

In step 14, in the actual operation, photometric data ($E_{ij}^0$) of the color negative film under a light source of an unknown type is obtained and a spectral reflectance (that is, $\alpha_{ik}$) minimizing the difference $\Delta E$ between the data $E_{ij}^0$ and the sensor output value $E_{ij}^Z$ is obtained, as expressed by Expression (10) given blow:

$$\Delta E = \sum_{i=1}^{n} \sum_{j=1}^{4} (E_{ij}^0 - E_{ij}^Z)^2 \qquad (10)$$

Here, this calculation can be done using the aforementioned many $E_{ij}^Z$ accumulated in the memory.

In step 16, the evaluation value V is calculated for the spectral reflectance minimizing $\Delta E$, and a light source type corresponding to the minimum value of the evaluation value V is estimated as the photographic light source.

In Table 1 given below, there is shown a point at which the minimum evaluation value V is obtained for each of the light source types in the three-signal system, the first four-signal system (X1 sensor is used), and the second four-signal system (X2 sensor is used).

TABLE 1

Light Source Whose Evaluation Value V Assumes Minimum Value

| Light Source Kind | 3 ch Input | 4 ch Input (645 nm) | 4 ch Input (675 nm) |
|---|---|---|---|
| Black Body 3000 K | 2765 K | 2805 K | 2814 K |
| 5000 K | 4419 K | 4510 K | 4541 K |
| 7000 K | 5900 K | 6021 K | 6127 K |
| 9000 K | 7187 K | 7384 K | 7572 K |
| Fluorescent Lamp F1 | F10 | F1 | F1 |
| F2 | F11 | F2 | F2 |
| F3 | F12 | F3 | F3 |
| F4 | F4 | F4 | F4 |
| F5 | F10 | F1 | F5 |
| F6 | F11 | F2 | F6 |
| F7 | 4497 K | 4973 K | F7 |
| F8 | 3687 K | 3679 K | F9 |
| F9 | F11 | 3218 K | F9 |
| F10 | 3722 K | F2 | F11 |
| F11 | 3155 K | F3 | F11 |
| F12 | F12 | F12 | F12 |

Table 1 shows how a certain light source type was discriminated using the light source type discriminating method according to this embodiment. For comparison, Table 1 also shows results of discrimination using the conventional method, that is, discrimination results in the case of the three-signal system where only the three R, G, and B sensors are used. As can be seen from the discrimination results concerning the fluorescent lamps F1 to F12, almost all of the light source types are correctly discriminated using the light source type discriminating method according to this embodiment.

Also, in the case of the three-signal system (denoted as "3ch input" in Table 1), the color temperature of a black body radiation light source, whose actual color temperature is 5000 K, is obtained as 4419 K, for instance. In contrast to this, when the X1 sensor is used (denoted as "4ch input (645 nm)" in Table 1), the color temperature is obtained as 4510 K. Further, when the X2 sensor is used (denoted as "4ch input (675 nm)" in Table 1), the color temperature is obtained as 4541 K. As can be seen from these results, an effect obtained is that the accuracy is improved also in estimation of a color temperature.

According to the example described above, the fourth sensor is introduced, so that there is provided an extremely remarkable effect that, when photometric data ($E_{ij}^0$) of a color negative film under a light source of an unknown type is obtained, it is possible to accurately discriminate the type of light source used to photograph images on the color negative film, including the fluorescent lamps.

It should be noted here that FIGS. 5 and 6 referred to when describing the indicators of the light source similarity correspond to the spectral sensitivity of a color negative film ("Superia 400" manufactured by Fuji Photo Film Co., Ltd.). Therefore, as another example, there will be next described a case of the spectral sensitivity of a digital still camera ("S1 pro" also manufactured by Fuji Photo Film Co., Ltd.).

Figure 12:
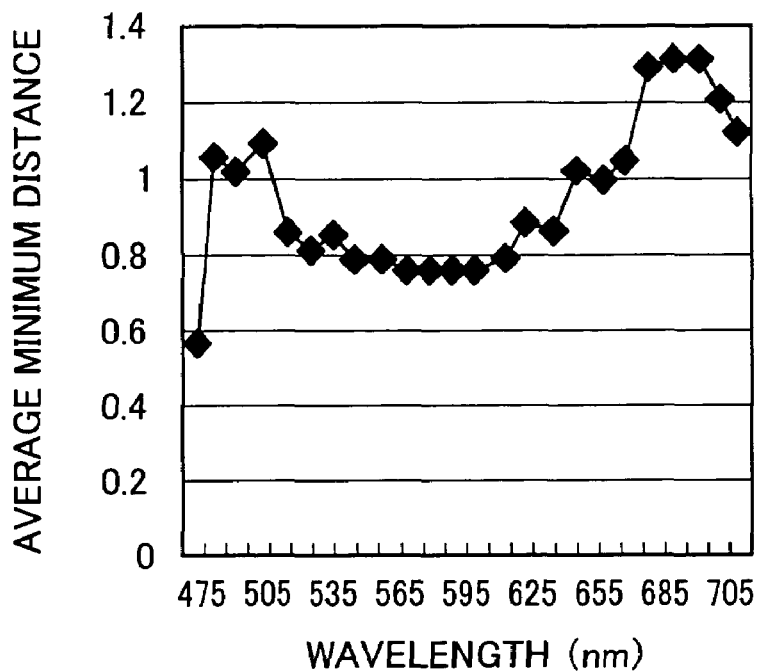
FIG. 12 is an explanatory diagram showing how the average minimum distance between the fluorescent lamps moves when the peak position (wavelength) of the spectral sensitivity of the X sensor is changed under a state where the spectral distribution is changed.
Figure 13:
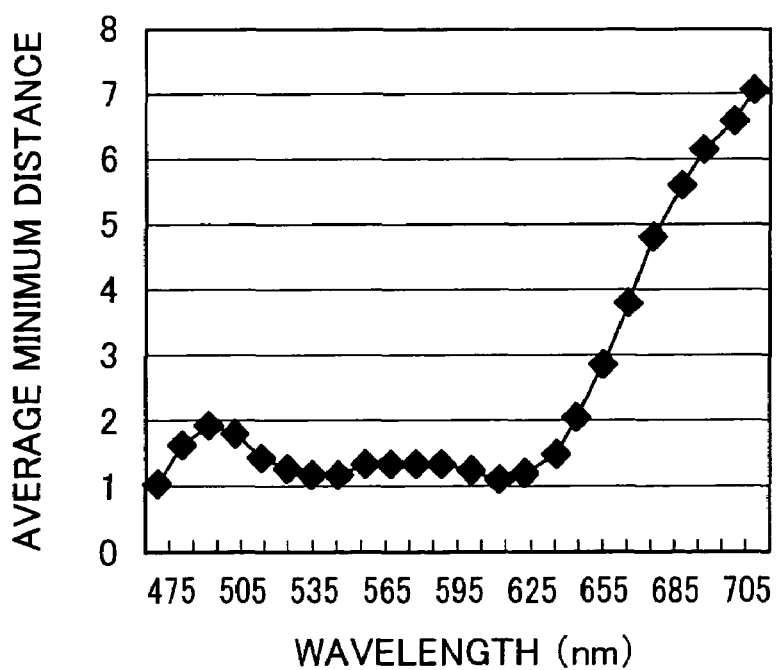
FIG. 13 is an explanatory diagram showing how the similarity changes when the peak position (wavelength) of the spectral sensitivity of the X sensor is changed under a state where the spectral distribution is changed under a state where the fluorescent lamps and the black body radiation light sources are included.

Although details are omitted, as shown in FIGS. 12 and 13, the optimum peak wavelength of the fourth sensor (X sensor) exists at 685 nm. Also, it was confirmed that this optimum peak wavelength hardly depends on the spectral sensitivities of the first to third sensors (R, G, B). From these results, it can be said that the optimum peak wavelength of the fourth sensor (X sensor) exists at a position displaced toward the long wave side by 30 nm or more from the absorption peak of the R sensor described above, and the absorption peak thereof exists in a region of 700 nm or less, more specifically, in the vicinity of 680 nm.

As still another example, a case where the shape of the spectral sensitivity of the sensor is changed will be described. In this example, the following conditions are combined. That is, the absorption peak of the sensor used is set at 680 nm and 515 nm, and the shape of the spectral sensitivity is changed (bandwidth is changed from 1.0 (unchanged) to 0.33 (⅓)). Also, there are considered two spectral sensitivities that are the spectral sensitivity of the aforementioned color negative film (Superia 400) and the spectral sensitivity of the digital camera (S1 pro).

It should be noted here that as the X sensor with the peak wavelength of 515 nm added in this example, there is selected and used a sensor shown in FIG. 5 which seems to have a high possibility that it may be used as the X sensor.

Figure 14:
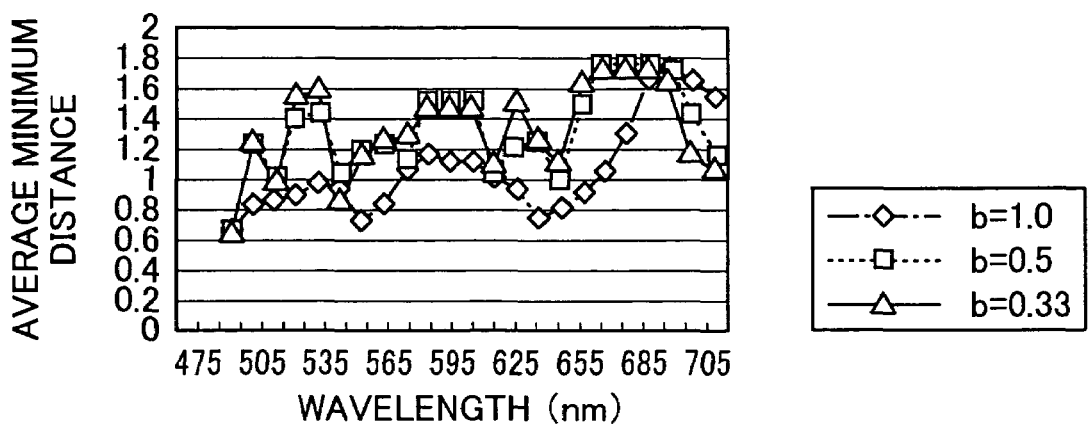
FIG. 14 is an explanatory diagram showing how the average minimum distance between the fluorescent lamps moves when the peak position (wavelength) of the spectral sensitivity of a fourth sensor (X sensor), whose peak wavelength is 515 nm, is changed under a state where the bandwidth of the X sensor is changed.
Figure 15:
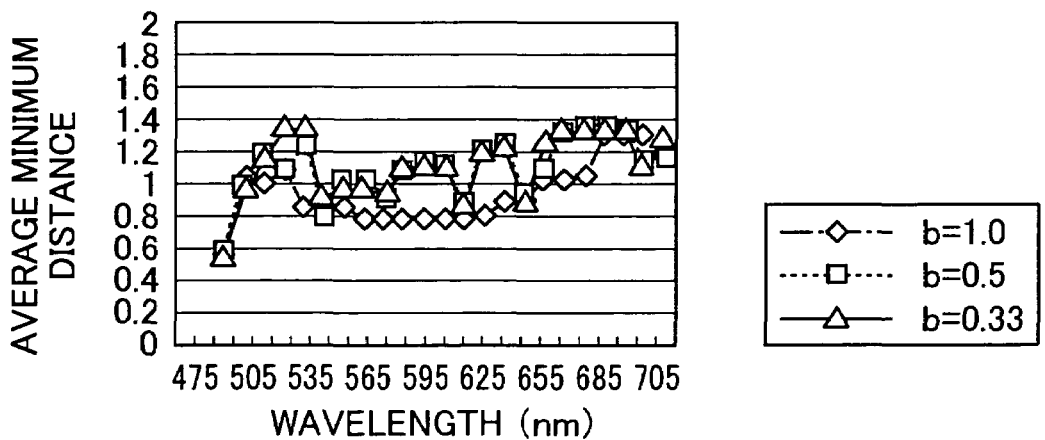
FIG. 15 is an explanatory diagram showing how the similarity changes when the peak position (wavelength) of the spectral sensitivity of the X sensor is changed under a state where the bandwidth of the X sensor is changed and the fluorescent lamps and the black body radiation light sources are included.

Although details are omitted, as can be seen from FIGS. 14 and 15, when the bandwidth of the fourth sensor (X sensor) whose peak wavelength is at 515 nm is set at 0.33 (⅓), the performance in detecting the similarity between light sources (average minimum distance described above) is improved as compared with a case where the bandwidth of the fourth sensor whose peak wavelength is at 515 nm is set at 1.0 (unchanged). Based on this fact, light source type estimating experiments were conducted by setting the peak wavelength and bandwidth of the fourth sensor (X sensor) at 515 nm and 0.33 (⅓), respectively.

The results of the experiments are shown in Table 2 given below.

TABLE 2

Light Source Whose Evaluation Value V Assumes Minimum Value

| Light SourceKind | ※1 4 ch (515 nm, b = 1.0) | ※1 4 ch (515 nm, b = 0.33) | ※2 4 ch (515 nm, b = 0.33) |
|---|---|---|---|
| Fluorescent Lamp F1 | F5 | F1 | F1 |
| F2 | F3 | F2 | F2 |
| F3 | F4 | F3 | F3 |
| F4 | F4 | F4 | F4 |
| F5 | F1 | F1 | F1 |
| F6 | F3 | F2 | F2 |
| F7 | 5635 K | 5237 K | 5146 K |
| F8 | 3798 K | 3851 K | 3911 K |
| F9 | 3558 K | 3441 K | 3475 K |
| F10 | F10 | F10 | F10 |
| F11 | F11 | F11 | F11 |
| F12 | F12 | F12 | F12 |

※1: Superia400
※2: S1pro

Table 2 shows how the performance in discriminating among the CIE fluorescent lamps is changed when the bandwidth of the X sensor having the peak wavelength of 515 nm is changed from 1.0 (unchanged) to 0.33 (⅓). Note that as to the case where the bandwidth is set at 0.33, another experiment was conducted on the spectral sensitivity of the digital camera (S1 pro) described above as a modification of the spectral sensitivity.

As can be seen from Table 2, when the bandwidth is narrowed, the performance in discriminating among the light source types is clearly enhanced (although partially). Note that in this experiment, no influence due to a difference in spectral sensitivity between the color negative film (Superia 400) described above and the digital camera (S1 pro) was observed.

According to this example, even when a sensor, whose peak wavelength is 515 nm and differs from that described above, is used as the fourth sensor, such an effect can be obtained that when the photometric data ($E_{ij}^0$) of a color negative film, on which images have been photographed under a light source of an unknown type, is obtained, it becomes possible to discriminate the type of photographic light source (in particular, the type of fluorescent light) used at the time of photographing on the color negative film with considerable accuracy.

Also, in FIGS. 14 and 15, when determining the peak wavelength of the fourth sensor (X sensor), a sensor having a larger average minimum distance is selected first. This determination may be performed with reference to the range of a target light source type, as will be described below.

For instance, as described above, when it is intended to discriminate among the 12 types of CIE fluorescent lamps in addition to the four types of black body radiation light sources with high precision, it is preferable that an average minimum distance is maintained around 1.2 or more. When the number of the light source types to be discriminated is smaller, even if the average minimum distance is set equal to or more than 1.0, or even set equal to or more than 0.8, it is possible to partially utilize the effect provided by the discriminating method according to the present invention.

Among the 12 types of CIE fluorescent lamps, there are some that are not actually used. Therefore, if it is possible to create or obtain data showing the frequency of use of each of the 12 types of fluorescent lamps, it becomes possible to determine the value of the average minimum distance described above based on the data. Thus, it is possible to determine the fourth sensor (X sensor) to be used, based on the determined value.

That is, as will be understood from the experiment results obtained using the light source type discriminating method according to the first aspect of the present invention, the essence of achieving the object of the present invention is that in addition to the sensors having spectral sensitivities corresponding to the three R, G, and B colors used for general analysis of a color image, a sensor having a narrow absorption peak band is arranged in another area such as a vacant area between the existing sensors.

It should be noted here that the light source type discriminating method according to the first aspect of the present invention is applicable to an exposure control device in a photographic printer, that is, an application is possible where the exposure time of the print is controlled based on the discriminated color temperature at the time of printing a print target image of a photographic film on a print sensitive material serving as a duplicating sensitive material. In this case, it is sufficient that the spectral sensitivity distribution $S_j(\lambda)$ of each sensor described above is replaced with the sensitivity distribution of the photographic film.

As described in detail above, according to the first aspect of the present invention, the fourth sensor is introduced, so that the remarkable effect can be obtained that a type of photographic light source can be discriminated among various light sources including fluorescent lamps with high precision.

The light source type discriminating method according to the first aspect of the present invention is basically constructed in the manner described above.

An image forming method according to a second aspect of the present invention will be described with reference to FIGS. 1 to 11.

The image forming method according to the second aspect of the present invention is based on the light source type discriminating method according to the first aspect of the present invention. Therefore, in the following description, the description of the method of estimating a type of photographic light source among various light sources including fluorescent lamps is omitted and only an embodiment of the image forming method according to the second aspect of the present invention will be described.

Hereinafter, description will be made of an image forming method in which input image data is reproduced as an image with a favorable color balance using the light source type discriminating method according to the first aspect of the present invention, that is, based on a light source type discriminated (estimated) using the light source estimating program disclosed in U.S. Pat. No. 5,636,143 and the four R, G, B, and X sensors described above.

The light source type estimated (discriminated) using the light source type discriminating method according to the first aspect described above is referred to as "ZE" and the light source type that should be reproduced is referred to as "Z0". As to the light source type Z0, when photographing is performed using a film for daylight photographing, photographing under a daylight light source matches the design and an image having a favorable color balance is obtained. In the following description, a black body radiation light source of around 5500 K is set as the aforementioned light source Z0 that should be reproduced.

A sensor output $E_{ij}^Z$ corresponding to a photographic light source Z is given by Expressions (6) and (7) described above. Here, it is assumed that as in the above description, the sensor output $E_{ij}^Z$ corresponding to each of various light sources Z is converted into a table and is accumulated in a memory in the advance preparation step of the light source type discriminating method according to the first aspect described above (see step 12 in FIG. 11).

It is also assumed that as to the estimated light source type ZE, a sensor output $Eij^{ZE}$ (j=R, G, B, X) is obtained for each color spectral sensitivity.

It is further assumed that as to the light source type Z0 that should be reproduced, a sensor output $Eij^{Z0}$ (j=R, G, B, X) is obtained for each color spectral sensitivity by referring to the table described above.

Under the conditions described above, as to the gray portion i (or an average portion when considered in terms of LATD) in the input image, a coefficient matrix, with which the sensor output $Eij^{ZE}$ (j=R, G, B, X) becomes the sensor output $Eij^{Z0}$ (j=R, G, B, X), is obtained using Expression (11) given below:

$$Ei^{Z0} = A \cdot Ei^{ZE} + C \text{ provided that} \tag{11}$$

$$Ei^{Z0} = \begin{vmatrix} EiR^{Z0} \\ EiG^{Z0} \\ EiB^{Z0} \\ EiX^{Z0} \end{vmatrix}, \quad Ei^{ZE} = \begin{vmatrix} EiR^{ZE} \\ EiG^{ZE} \\ EiB^{ZE} \\ EiX^{ZE} \end{vmatrix}$$

where A and C are each a coefficient matrix.

In more detail, calculation is performed using Expression (12) given below:

$$\begin{vmatrix} EiR^{Z0} \\ EiG^{Z0} \\ EiB^{Z0} \\ EiX^{Z0} \end{vmatrix} = \begin{vmatrix} AR & 0 & 0 & 0 \\ 0 & AG & 0 & 0 \\ 0 & 0 & AB & 0 \\ 0 & 0 & 0 & AX \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \tag{12}$$

Here, the coefficient C may be zero.

Also, the minimum number of elements in the expressions described above may be three colors. When ordinary photographing is performed and sensitivities concerning three colors that are R, G, and B exist, the item "X" is not necessary.

In this case where the coefficient matrix A is a diagonal matrix, the sensitivity ratios among the spectral sensitivities of respective colors are adjusted in accordance with differences in light source type. This means that the gray balance is adjusted.

As a result of the conversion processing described above, an image subjected to balance adjustment (that is, an image photographed under the light source Z0) is calculated from an obtained image (that is, an image under the light source ZE).

In order to output the image, whose balance has been adjusted, as an actual image, various types of color signal processing and the like may be performed on the signal of the image having been subjected to the balance adjustment.

For instance, it is possible to perform device-dependent color signal conversion for obtaining an appropriate output. Also, the image signal having been subjected to the balance adjustment may be dealt with as exposure density through logarithmic processing and be converted into a density signal to be applied to creation of a print using a photosensitive material having superior color reproducibility. Note that it is also effective to combine them with each other.

Also, in the above description, an example was given where a photosensitive material (color negative film) is used as a photographing material. However, the present invention is not limited to this and it is possible to deal with the spectral sensitivity characteristics of a so-called digital camera (DSC) in completely the same manner.

As to the conversion expression described above, there has been described a case where the coefficient matrix A is a diagonal matrix. However, in the second aspect of the present invention, it is also possible to perform the color conversion in the case where the coefficient matrix A has non-diagonal components (see Expression (13) given below).

$$\begin{vmatrix} EiR^{Z0} \\ EiG^{Z0} \\ EiB^{Z0} \\ EiX^{Z0} \end{vmatrix} = \begin{vmatrix} AR_1 & AR_2 & AR_3 & AR_4 \\ AG_1 & AG_2 & AG_3 & AG_4 \\ AB_1 & AB_2 & AB_3 & AB_4 \\ AX_1 & AX_2 & AX_3 & AX_4 \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \tag{13}$$

In this case, it is sufficient that the coefficient matrices A and C are obtained for data containing abundant colors exemplified by the Macbeth color checker. The subsequent processing is performed in the same manner as in the example described above. In such a case, an effect obtained is that color matching can be performed even for colors other than the gray portion.

Also, a case where linear conversion is performed on signals as color correction has been described above. However, it is possible to use a conversion matrix where consideration is given to signal components of the order 2 or more without departing from the scope of the image forming method according to the second aspect of the present invention.

Further, in order to retain the atmosphere of a photographic light source, the execution of an interior-division operation on the sensor output $Eij^{Z0}$ (j=R, G, B, X) obtained with Expression (11) and the sensor output $Eij^{ZE}$ (j=R, G, B, X) of the photographic light source is effective in some cases. It is possible to carry out this operation within the scope of the image forming method according to the present invention.

As the color conversion processing described above, for instance, it is possible to apply various types of processing that are disclosed in JP 11-177832 A titled "Image Processing Method and Device therefor", JP 2000-137305 A titled "Method and Device for correcting color", and the like pertaining to one of the inventors of the present invention.

As described in detail above, according to the second aspect of the present invention, the discrimination (estimation) of a light source type is performed using at least a part of reflection light from a light source whose light source type is to be discriminated. After that, image data conversion is performed based on a color conversion method defined by the sensor outputs obtained with this estimated light source type and a desired (reference) light source type. As a result, a remarkable effect obtained is that it becomes possible to realize an image forming method in which appropriate image processing can be performed based on the type of photographic light source, that is, a result of the light source type estimation.

The image forming method according to the second aspect of the present invention is basically constructed in the manner described above.

A method and apparatus for estimating a light source energy distribution according to a third aspect of the present invention, and an exposure amount determining method according to a fourth aspect will be described below with reference to FIGS. 3, 9, and 16 to 30.

First, an operation according to the third aspect of the present invention will be described.

If the spectral energy distribution of a photographic light source is referred to as $P(\lambda)$, the spectral sensitivity distribution of a film used for photographing is referred to as $S(\lambda)$, and the spectral reflectance distribution of a subject to be photographed is referred to as $\rho(\lambda)$, exposure amount data $E$ can be expressed with Expression (14) given below:

$$E = \int P(\lambda)\rho(\lambda)S(\lambda)d\lambda \qquad (14)$$

However, the spectral reflectance distribution of the subject differs from image to image at the time of photographing, so that it is impossible to specify the spectral reflectance distribution. Therefore, it is difficult to estimate the spectral energy distribution and the like of the photographic light source from the images on a film, as described above.

In contrast to this, with the light source spectral energy distribution estimating method according to the third aspect and the fourth aspect of the present invention, as to the spectral energy distribution of a light source having an unknown spectral energy distribution, main component vectors are obtained based on a result of main component analysis of each type of known light source called a standard light source, the main component vectors are set as $v_j(\lambda)$, and the spectral spectrum distribution of the light source is generated in accordance with Expression (15) given below:

$$P(\lambda) = \sum_{k=1}^{k} b_n \cdot v_n(\lambda) \qquad (15)$$

where $P(\lambda)$ is the spectral energy distribution of the light source, $b_n$ is the weighting coefficient of the main component, k is a value showing the k-th component until which the main component vectors are used, and $v_n(\lambda)$ is the main component vector.

In this embodiment, k weighting coefficients $b_n$ are changed in various manners, thereby generating the light source spectral energy distribution $P(\lambda)$ in accordance with Expression (15) described above. As to the light source spectral energy distribution $P(\lambda)$ generated in this manner, an evaluation value V is obtained in the method disclosed in U.S. Pat. No. 5,636,143 described above. As to the obtained evaluation value V, a weighting coefficient $b_n$ giving the smallest V value is obtained.

Then, as to the weighting coefficient $b_n$ giving the smallest V value, the light source spectral energy distribution is calculated in accordance with Expression (15) given above, and it is estimated that the obtained light source spectral distribution is the spectral distribution of the light source used at the time of photographing.

Up to this point, we have provided an overview of an operation according to the third aspect and the fourth aspect of the present invention. In more detail, the calculation is performed as follows.

Here, it is assumed that there exists sensor output value data ($E_{ij}^0$) in the case where a subject illustrated with light from a light source having an unknown spectral energy distribution is photographed, and the spectral energy distribution of the light source used at the time of recording the subject is to be obtained. In this case, the data $E_{ij}^0$ and the weighting coefficient $b_n$ described above are changed in various manners and there is found a light source having a spectral energy distribution minimizing the difference $\Delta E$ with the sensor output value $E_{ij}^T$ corresponding to the spectral energy distribution $P(\lambda)$ of the light source generated in accordance with Expression (15) described above. This calculation is performed in accordance with Expression (16) given below:

$$\Delta E = \sum_{i=1}^{n} \sum_{j=1}^{3} (E_{ij}^0 - E_{ij}^T)^2 \qquad (16)$$

where $E_{ij}^0$ is the sensor output of the image data and $E_{ij}^T$ is the sensor output corresponding to the spectral energy distribution of the light source generated with each $b_n$.

As a model of the calculation for minimizing $\Delta E$ expressed by Expression (16) described above, the main component analysis was applied to the light source spectral spectrums of 18 types of light sources, that is, JISZ8720 standard light A, D65, and C, JISZ8720 auxiliary standard light D50, D55, and D75, and 12 types of fluorescent lamps described in JISZ8719. In this manner, their main component vectors were obtained.

Figure 16:
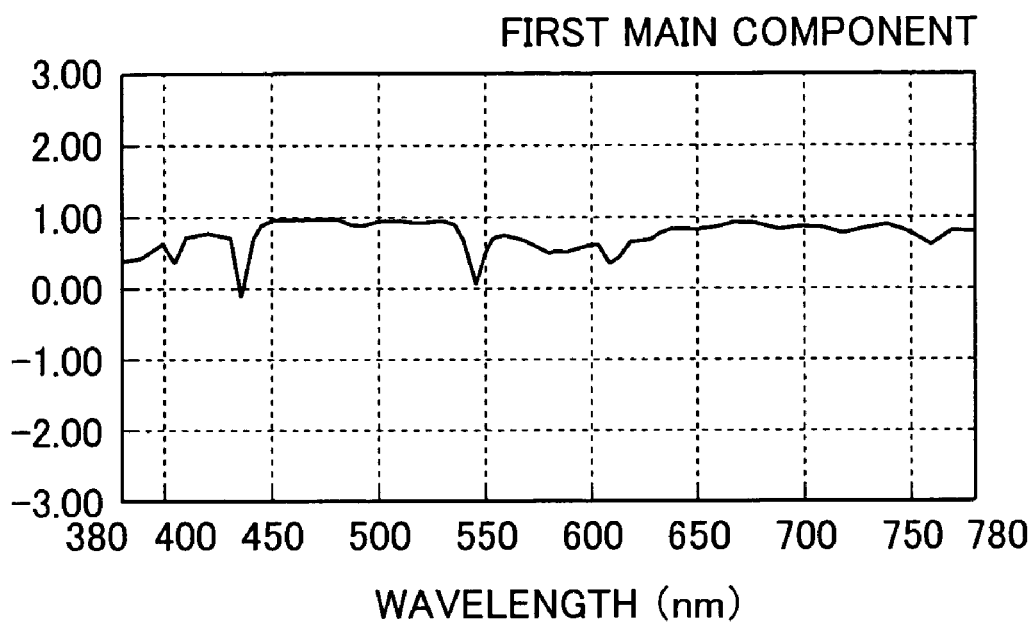
FIG. 16 shows a first example of a main component vector used in the present invention.
Figure 17:
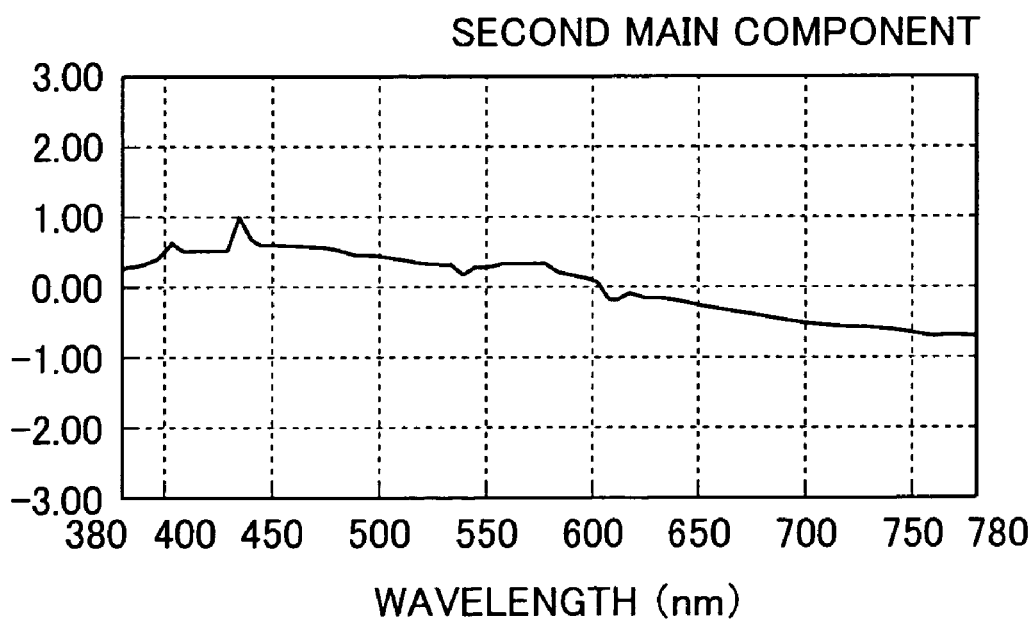
FIG. 17 shows a second example of the main component vector used in the present invention.
Figure 18:
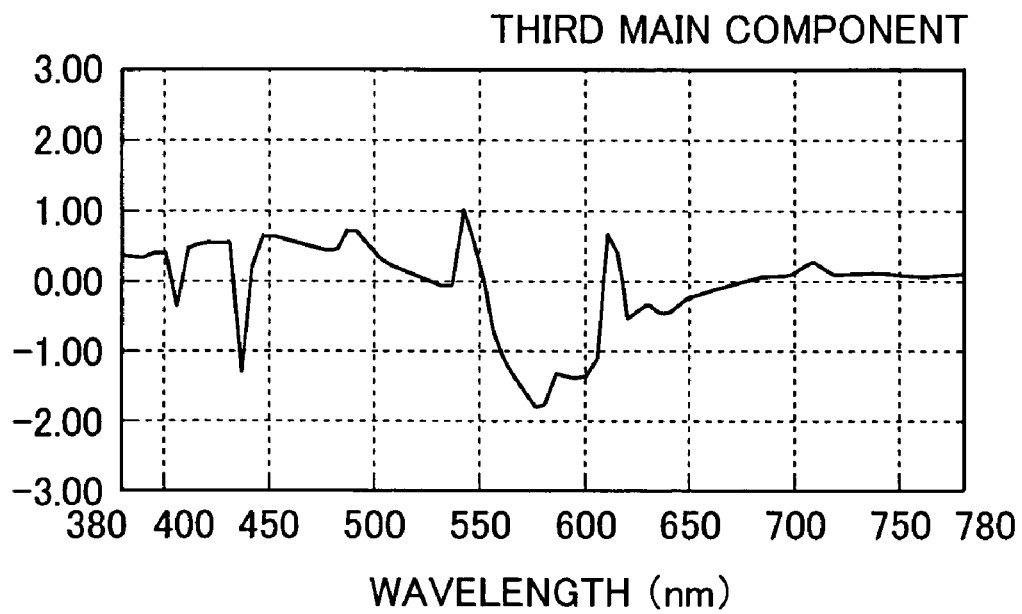
FIG. 18 shows a third example of the main component vector used in the present invention.
Figure 19:
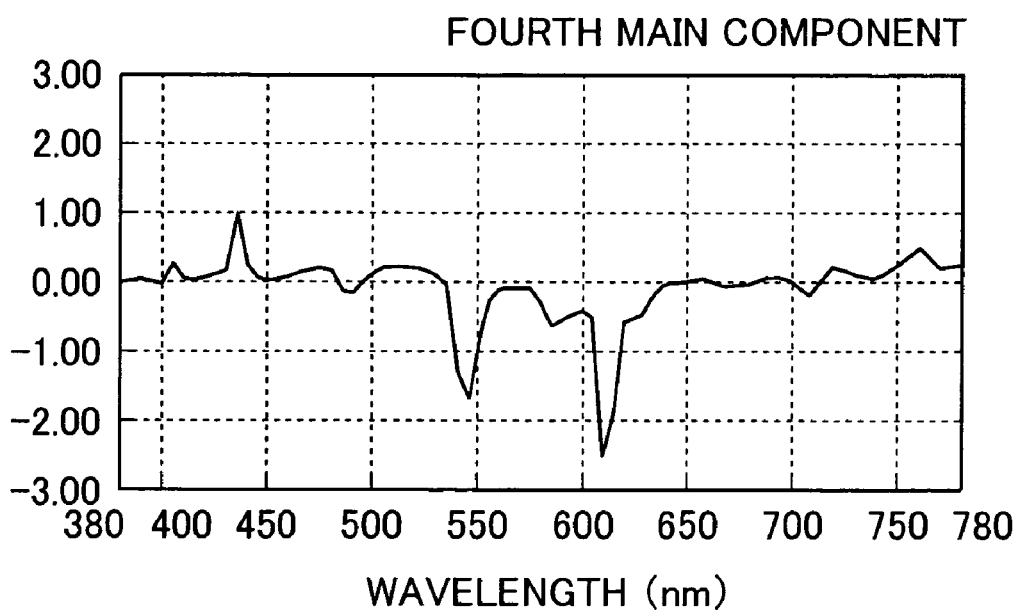
FIG. 19 shows a fourth example of the main component vector used in the present invention.
Figure 20:
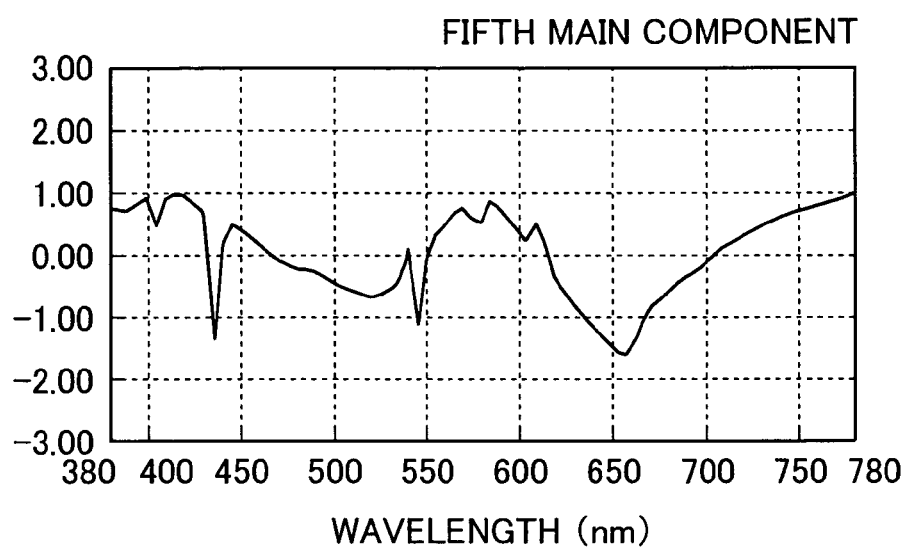
FIG. 20 shows a fifth example of the main component vector used in the present invention.

The characteristics of the main components are shown in FIGS. 16 to 20. Note that FIG. 16 shows a first main component, FIG. 17 shows a second main component, FIG. 18 shows a third main component, FIG. 19 shows a fourth main component, and FIG. 20 shows a fifth main component.

As to the main component vectors obtained in this manner, the spectral spectrum distributions of various light sources are generated in accordance with Expression (15) described above.

Then, the k weighting coefficients $b_j$ described above are changed in various manners, thereby generating many light source spectral distributions $P(\lambda)$ in accordance with Expression (15) described above. As to the light source spectral energy distributions $P(\lambda)$ generated in this manner, the minimization of $\Delta E$ in Expression (16) described above was performed with respect to a case where 24 colors of the Macbeth chart were used as a subject. Here, the data $E_{ij}^0$ is obtained using the spectral sensitivity of an actual film and an actually measured spectral reflectance from Expression (17) given below obtained by modifying Expression (14).

$$E_{ij}^0 = \int P(\lambda)\rho_i(\lambda)S_j(\lambda)d\lambda \qquad (17)$$

where $P(\lambda)$ is the spectral energy distribution of the light source, $\rho_i(\lambda)$ is the spectral reflectance of the subject and $S_j(\lambda)$ is the spectral sensitivities of the sensors (=R, G, B).

By the way, the light source spectral energy distributions $P(\lambda)$ corresponding to various $b_n$ values contain light source spectral energy distributions exhibiting an abnormal value of the spectral reflectance of the restored subject in some cases. That is, there is a case where the obtained spectral reflectance $\rho_i(\lambda)$ becomes a negative value or greatly exceeds 1.0.

The spectral reflectance $\rho_i(\lambda)$ will never become a negative value or exceed 1.0 (that is, $0 \leq \rho_i(\lambda) \leq 1$), so that it is conversely possible to assume that the spectral energy distribution $P(\lambda)$ of the light source that is the cause of this abnormal spectral reflectance $\rho_i(\lambda)$ departs from the spectral energy distribution $P(\lambda)$ of a "true" light source.

Therefore, there is introduced an evaluation value V expressed by Expression (18) given below:

$$V = \sum_{i=1}^{n} (\text{MAX}[\rho_i(\lambda)] - 1.0) \qquad (18)$$

where $\rho i(\lambda)$ is the spectral reflectance of the subject restored from the spectral energy distribution of the light source. Here, it is assumed that V is set at 0 when the value inside the parentheses is negative.

Then, this evaluation value V is calculated for the light source spectral energy distributions $P(\lambda)$ corresponding to various $b_n$ values, and the spectral energy distribution $P(\lambda)$ of a light source corresponding to a combination of $b_n$ minimizing this evaluation value V is estimated as the spectral energy distribution $P(\lambda)$ of a light source that was actually used at the time of photographing.

In FIGS. 21 to 24, the light source spectral energy distributions obtained in the method described above and the "true" spectral energy distribution of the light source that was actually used when performing photographing on a target film are shown for comparison.

Note that in these drawings, a case where the main component vectors of the first to third main components are used and a case where the main component vectors of the first to fifth main components are used are shown for comparison.

Figure 21:
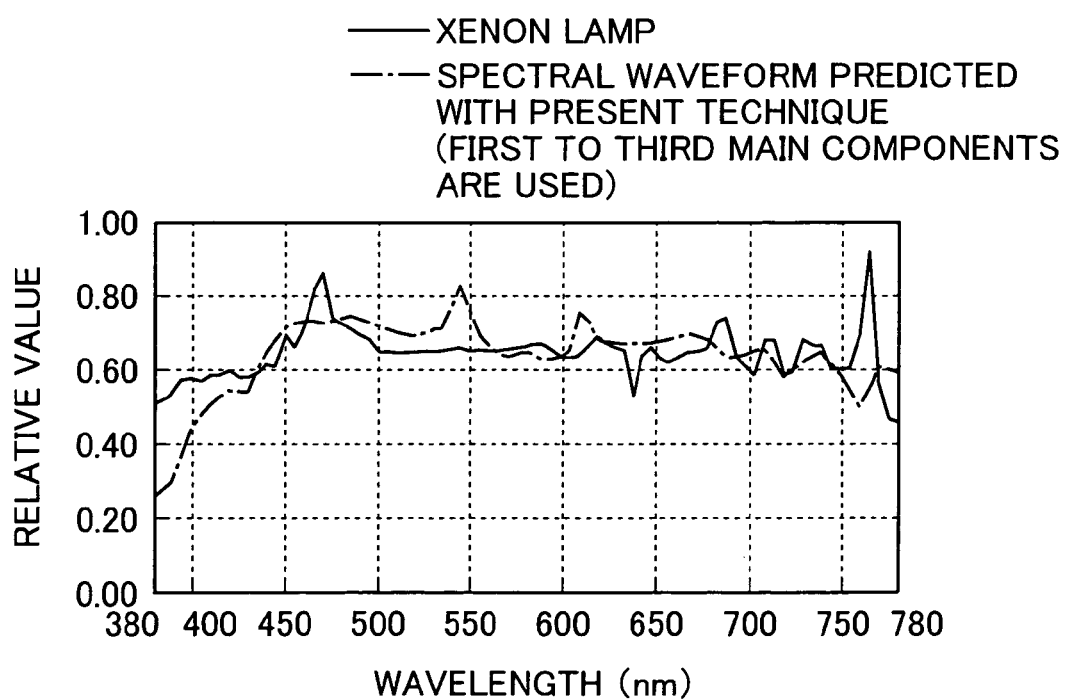
FIG. 21 is a first comparison diagram between the spectral energy distribution of an estimated light source and measurement values of an actual light source according to another embodiment of the present invention.

First, in FIG. 21, the spectral energy distribution of a general xenon lamp (specified by a solid line) is compared with an "estimated" light source spectral energy distribution (specified by an alternate long and short dashed line) obtained by applying the estimating method according to the present invention to the images photographed on a film. Note that the main component vectors of the first to third main components are used in this case.

Figure 23:
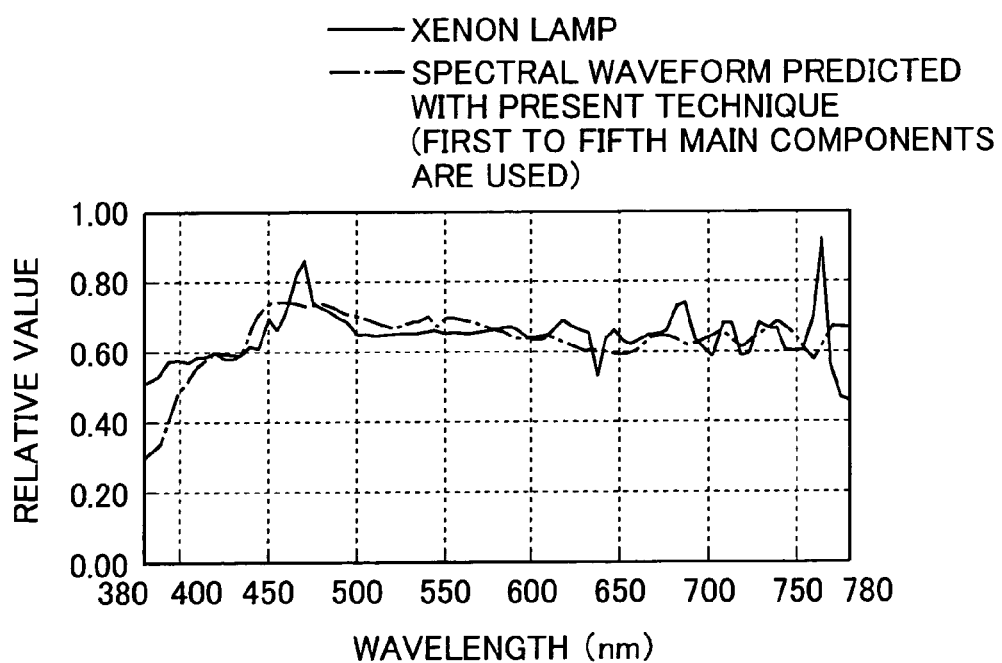
FIG. 23 is a third comparison diagram between the spectral energy distribution of the estimated light source and the measurement values of the actual light source in the embodiment.

FIG. 23 is the same as FIG. 21 except that the main component vectors of the first to fifth main components are used. As is apparent from the comparison between these drawings, when the main component vectors of the first to the fifth main components are used (FIG. 23), the matching degree between the actual characteristics and the estimation result is somewhat improved from the case where only the main component vectors of the first to third main components are used (FIG. 21). However, even if only the main component vectors of the first to third main components are used, it is sufficient for practical use.

Figure 22:
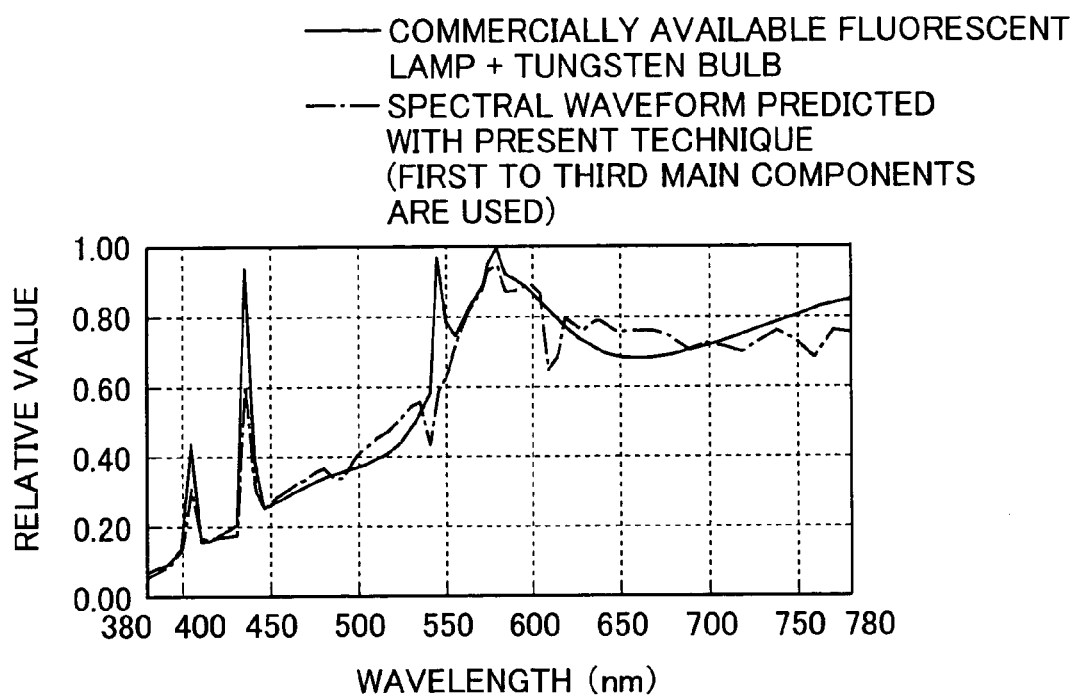
FIG. 22 is a second comparison diagram between the spectral energy distribution of the estimated light source and the measurement values of the actual light source in the embodiment.
Figure 24:
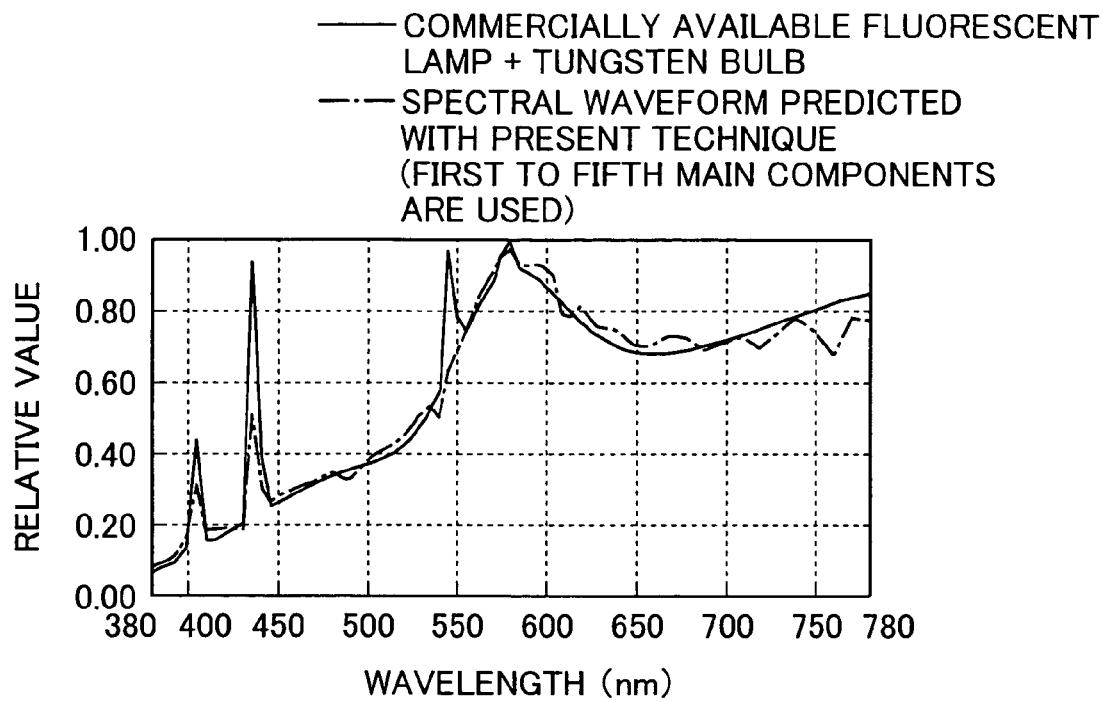
FIG. 24 is a fourth comparison diagram between the spectral energy distribution of the estimated light source and the measurement values of the actual light source in the embodiment.

Next, FIGS. 22 and 24 each show a case where photographing was performed using both of a commercially available fluorescent lamp and a tungsten bulb. In these drawings, the solid line specifies the spectral energy distribution obtained under a state where these two light sources were both used, while the alternate long and short dashed line specifies the spectral energy distribution of the "estimated" light source obtained using the estimating method according to the present invention.

It should be noted here that FIG. 22 shows a case where the main component vectors of the first to third main components are used, while FIG. 24 shows a case where the main component vectors of the first to fifth main components are used. Like in the case of FIGS. 21 and 23, when the main component vectors of the first to fifth main components are used (FIG. 24), the matching degree between the actual characteristics and the estimated result is somewhat improved from the case where only the main component vectors of the first to third main components are used (FIG. 22). However, even if only the main component vectors of the first to third main components are used, it is sufficient for practical use.

Figure 25:
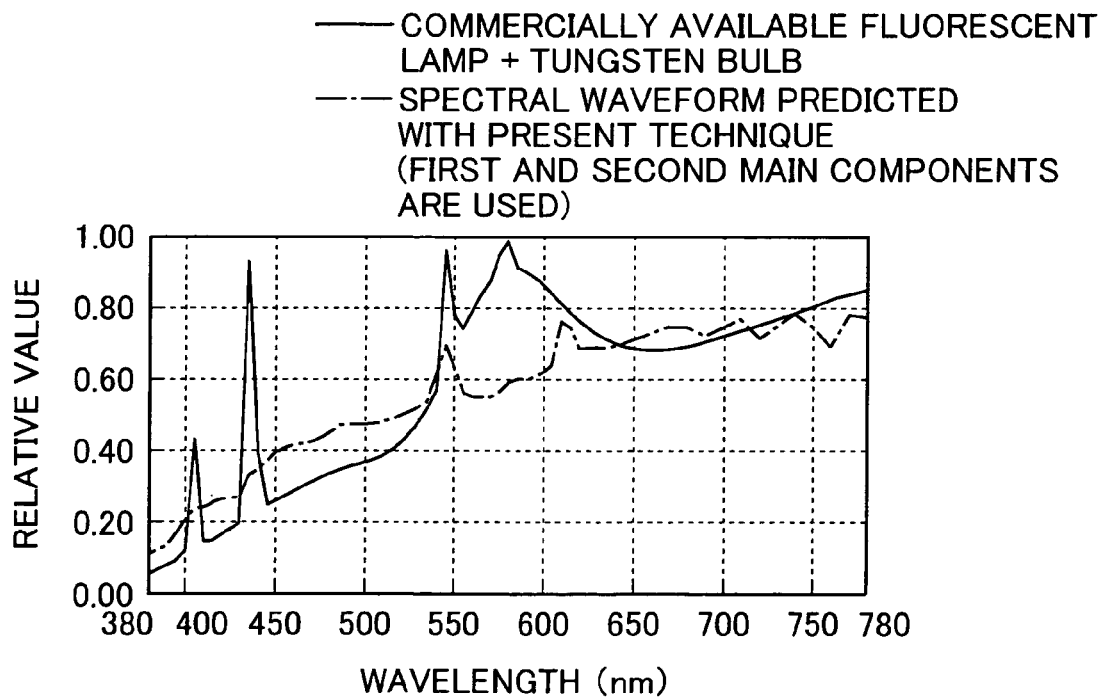
FIG. 25 is a fifth comparison diagram between the spectral energy distribution of the estimated light source and the measurement values of the actual light source in the embodiment.

Next, for reference purposes, FIG. 25 shows a result of a case where the light source spectral energy distribution is estimated in the method according to the present invention using the main component vectors of the first and second main components under the conditions shown in FIGS. 22 and 24.

As is apparent from FIG. 25, if the estimation is performed using only the main component vectors of the first and second main components, it becomes impossible to attain sufficient estimation accuracy and it is difficult to say it has a practical use.

From the results described above, in the method of estimating the spectral energy distribution of a photographic light source according to the third aspect of the present invention, it is preferable that the estimation is performed using the main component vectors of at least the first to third main components. It is more preferable that the estimation is performed using the main component vectors of the first to fifth main components.

Information on the light source spectral energy distribution obtained in the manner described above in the method of estimating the spectral energy distribution of a photographic light source according to the third aspect of the present invention is applicable to the control of a print exposure time at the time of photographic printing, that is, to the exposure amount determining method according to the fourth aspect of the present invention.

Figure 26:
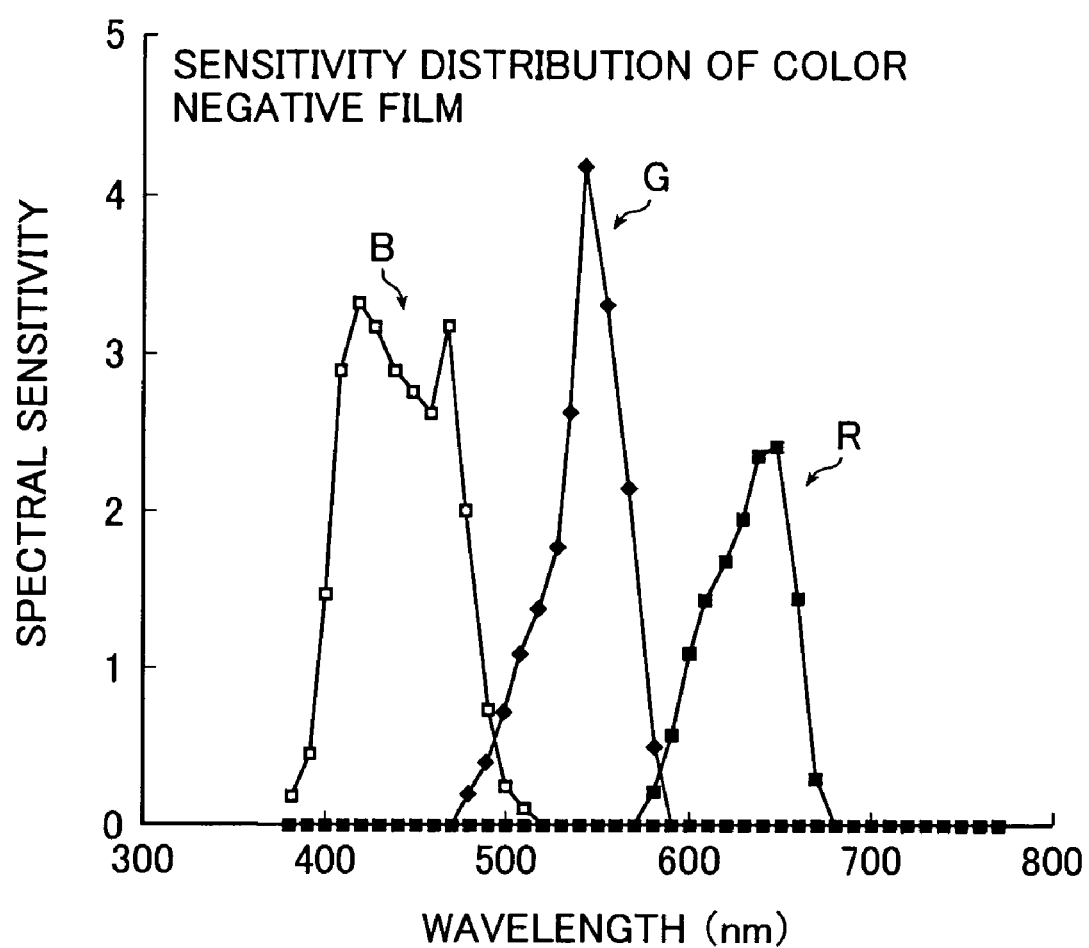
FIG. 26 shows an example of the spectral sensitivity distribution of a color negative film.

It should be noted here that if it is assumed that the exposure time of a print is controlled based on the type of light source having the thus estimated spectral energy distribution when a film image to be printed is printed on a print sensitive material serving as a duplicating sensitive material (exposure amount determining method), the spectral sensitivity distribution $S_j(\lambda)$ of the sensor may be replaced with the sensitivity distribution of the film, that is, for instance, the sensitivity distribution of a color negative film shown in FIG. 26.

Here, the spectral energy distribution of the light source for photometrically determining a color development density of the film and the spectral sensitivity distribution of the print sensitive material are previously determined through measurement. Thus, if the spectral transmission distribution of a film differing from film to film is determined, it becomes possible to obtain a density photometrically determined by a photometer having the same spectral sensitivity distribution as the print sensitive material. This technology is also described in JP 04-310942 A as a method of estimating the spectral distribution of a film.

Hereinafter, a concrete example will be described.

EXAMPLE 2

In this example, the exposure amount determining method according to the fourth aspect of the present invention is applied to an automatic printer.

Figure 27:
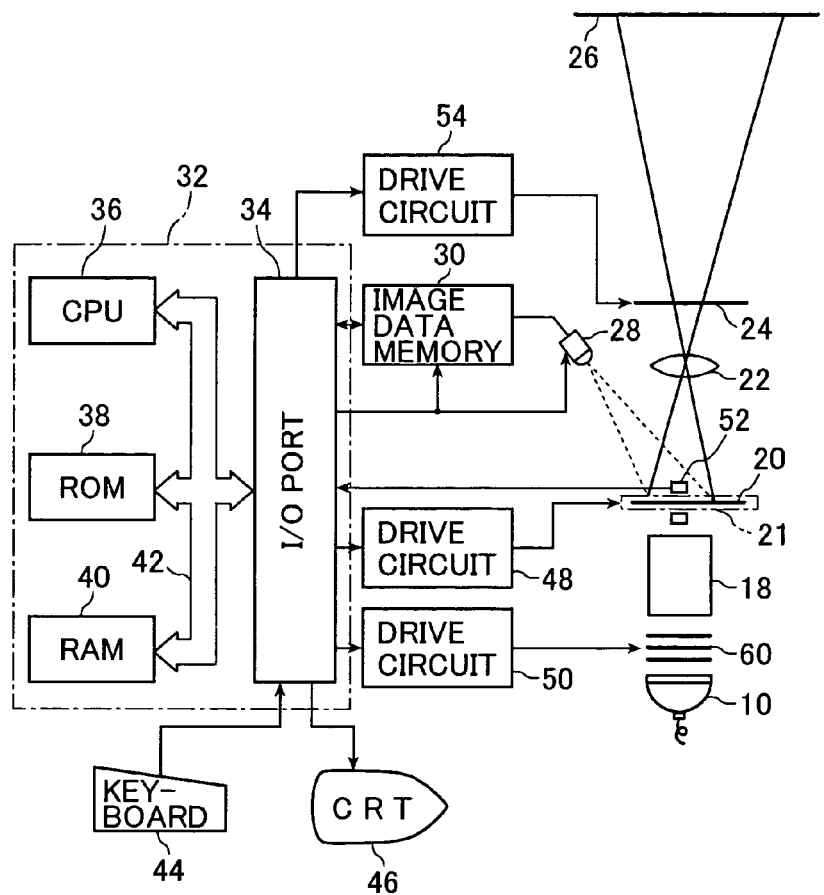
FIG. 27 is a schematic diagram of an automatic printer of another example of the present invention to which a result of light source spectral energy distribution estimation is applied.

FIG. 27 is a schematic diagram of an automatic printer which prints a photograph using a printing method (exposure amount determining method) based on the estimated light source spectral energy distribution described above.

A mirror box 18 and a lamp house 10 equipped with a halogen lamp are disposed below a color negative film 20 loaded in a negative carrier 21 and transferred to a printing section. A light adjusting filter 60 is interposed between the mirror box 18 and the lamp house 10. As is well known, the light adjusting filter 60 is formed by three filters, i.e., a yellow (Y) filter, a magenta (M) filter, and a cyan (C) filter.

A lens 22, a black shutter 24, and color paper 26 are disposed above the negative film 20 in this order. Light emitted from the lamp house 10 and passed through the light adjusting filter 60, the mirror box 18, and the color negative film 20 forms an image on the color paper 26 by means of the lens 22.

A DX code that represents the type of the color negative film is recorded in a side edge portion of the color negative film 20, with notches being formed along the side edges of the film. To detect the DX code and the notches, a detector 52 including a light-emitting element and a light-receiving element is disposed in such a way that the side edges of the negative film 20 are sandwiched between these elements.

A photometer 28 is disposed, in a direction inclined with respect to the optical axis of the above-described imaging optical system, and at a position where the photometer 28 can measure the density of the image on the color negative film 20. The photometer 28 is formed by three filters, which respectively have central wavelengths of 450±5 nm, 550±5 nm, and 700±5 mm and half-widths of 15 to 50 nm, and a two-dimensional imaging sensor. The light passed through the color negative film is separated into three wavelength bands and measured by the photometer 28.

The photometer 28 is connected to an exposure amount determining device 32 including a microcomputer via an image data memory 30 in which image data obtained by photometry with the photometer 28 is stored. The exposure amount determining device 32 includes an I/O port 34, a central processing unit (CPU) 36, a read only memory (ROM) 38, a random access memory (RAM) 40, and a bus 42 composed of a data bus for connecting these elements with each other, a control bus, and the like.

Figure 28:
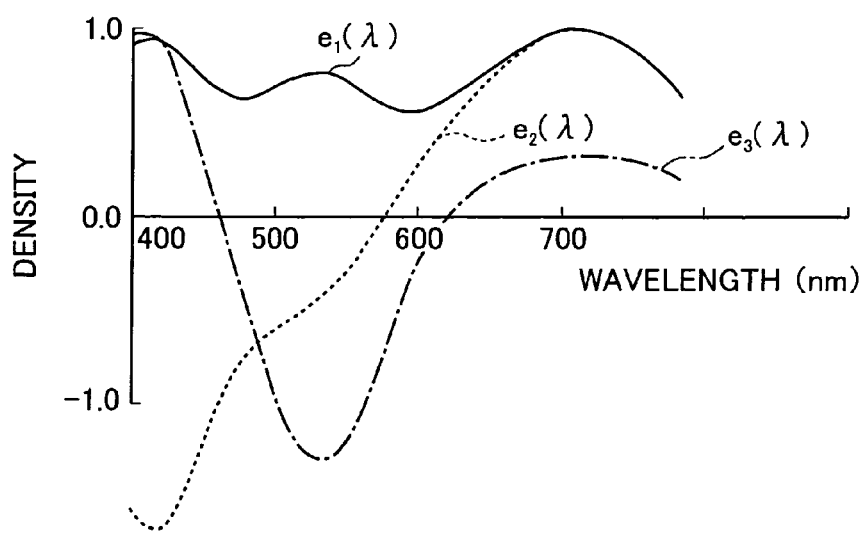
FIG. 28 shows an example of the spectral distributions of eigenvectors of a color negative film.

An exposure amount control routine program to be described later and distributions of eigenvectors $e_1$ ($\lambda$), $e_2$ ($\lambda$), and $e_3$ ($\lambda$) of a color negative film shown in FIG. 28 are stored in the ROM 38 for each type of film. Although FIG. 28 shows the distributions of eigenvectors for one type of film, it should be noted that substantially the same distribution is obtained for other types of film. Moreover, in the ROM 38, there are previously stored the spectral energy distribution of the halogen lamp provided in the lamp house 10, the spectral sensitivity distribution of paper used in the printer, and three spectral sensitivity distributions of the photometer corresponding to the transmission wavelength ranges of the three filters described above.

In order to change the paper to be used, spectral sensitivity distributions of multiple types of paper may be previously stored in the ROM, and the spectral sensitivity distribution of paper to be used may be selected with a keyboard 44. Alternatively, the spectral sensitivity distribution of required paper, which is stored in an external memory, such as a flexible disk, may be read into the RAM. Furthermore, it is also preferable that the spectral energy distribution of a lamp may be changed when the lamp is replaced.

To this end, the spectral energy distribution of the lamp may be photometrically determined by the photometer 28 directly or through a filter and the thus determined spectral energy distribution may be stored in the memory, or the spectral energy distribution of the lamp may be constantly corrected using a dedicated lamp monitoring sensor. In addition, the spectral sensitivity distribution of the color negative film (see FIG. 26), the eigenvectors of a subject (see FIG. 3), and the like are stored in the ROM 38.

The exposure amount determining device 32 is connected to the image data memory 30 so as to control the read and write timings of the image data memory 30 and to actuate the photometer 28. The I/O port 34 is connected to the negative carrier 21 via a drive circuit 48, to the light adjusting filter 60 via a drive circuit 50, and to the black shutter 24 via a drive circuit 54. The I/O port 34 is also connected to the keyboard 44, the detector 52, and a CRT 46.

Figure 29:
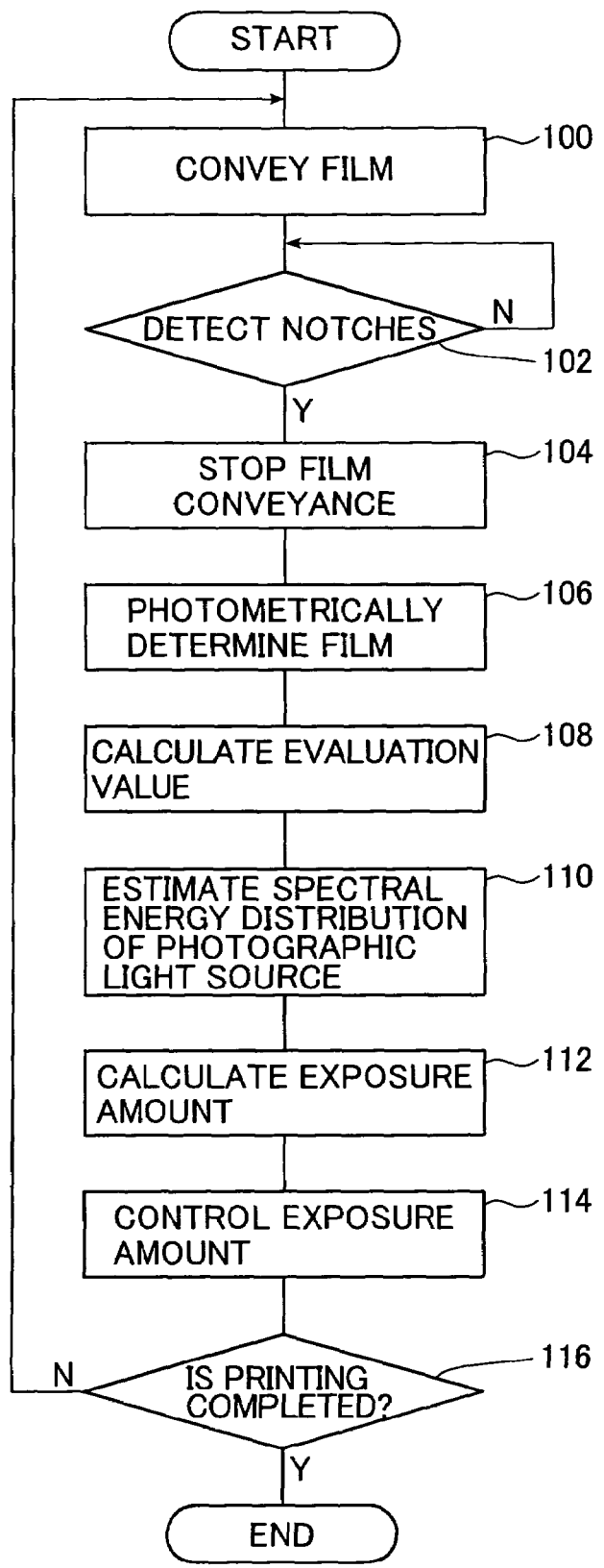
FIG. 29 is a flowchart of an exposure amount control routine of another example of the present invention.
Figure 30:
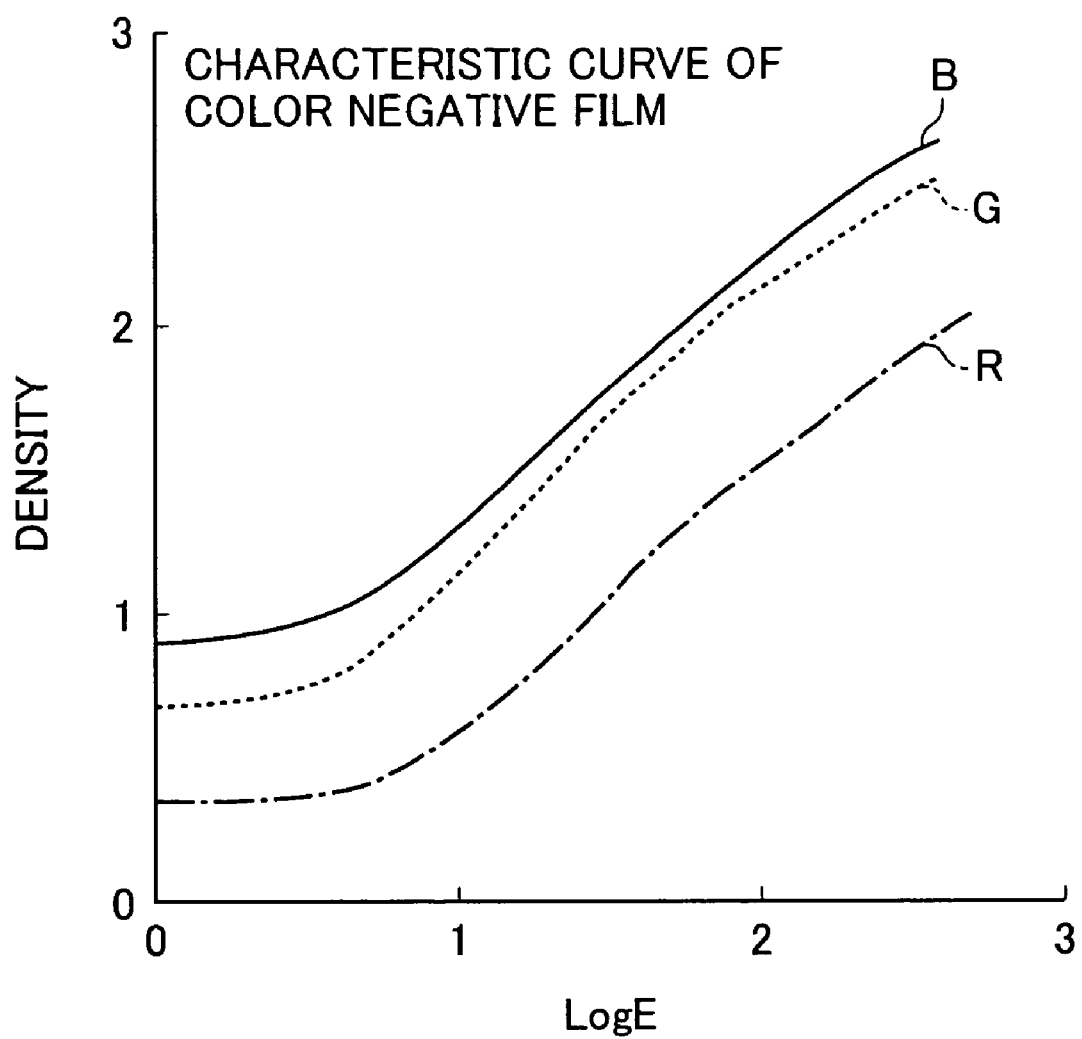
FIG. 30 shows a color negative film density-exposure amount characteristic curve.

The exposure amount control routine previously stored in the ROM 38 of the exposure amount determining device 32 will now be described with reference to FIG. 29. When the color negative film 20 is loaded in the negative carrier 21 and a start switch is turned on, the negative carrier 21 is actuated by the drive circuit 48 in step 100. As a result of this operation, the color negative film 20 is conveyed. While the color negative film 20 is being conveyed, the detector 52 reads the DX code and detects the notches.

In subsequent step 102, it is judged whether or not the detector 52 detected the notches. If it is judged that the notches were detected, the conveyance of the color negative film 20 is stopped in step 104, thereby causing a frame image on the color negative film 20 to stop at a position for exposure and printing. In step 106, a transmission density of the negative film 20 is photometrically determined by actuating the photometer 28. Because the photometer 28 is provided with the three filters, the transmission density of the negative film is spectrally divided into three wavelength bands and is photometrically determined.

In subsequent step 108, the type of film is distinguished with reference to the read DX code, and the spectral sensitivity distribution of the color negative film corresponding to the film of the distinguished type is read from the ROM. The previously mentioned evaluation value V is obtained by the use of a value photometrically determined by the photometer 28, the spectral energy distribution of the estimated light source, and the spectral sensitivity distribution of the color negative film.

In other words, the weighting coefficient $b_n$ that minimizes the difference $\Delta E$ is obtained using Expression (16) described above. A spectral reflectance is restored by Expression (17) described above using the thus obtained weighting coefficient $b_n$. The evaluation value V is obtained from Expression (18) using the thus restored spectral reflectance. The photometric value obtained by the photometer 28 and actually used as a sensor output value is a transmission density value of the negative film. Therefore, an exposure amount is calculated using a film density-exposure amount characteristic curve shown in FIG. 30 and is used to restore a spectral reflectance.

In step 110, as previously described, the light source spectral energy distribution at which the thus obtained evaluation value V becomes minimum is estimated.

In step 112, an exposure amount is calculated on the basis of the color temperature of the photographic light source estimated in step 110. Then, exposure amount control is executed based on the thus calculated exposure amount by controlling the light adjusting filter 60 in step 114.

After completion of the exposure amount control by the light adjusting filter 60 in step 114, the process proceeds to step 116 in which it is judged whether or not printing of all frames is completed. If the printing is not yet completed, the process returns to step 100 and the above-described steps are repeated. On the other hand, if the printing is completed, the routine is ended.

In the above example, by constructing a system using the exposure amount determining device 32 and photometer means including the photometer 28 and the image data memory 30, and by using this system to execute the above mentioned exposure amount control routine up to step 110, this system will function also as an apparatus that outputs the spectral energy distribution of a photographic light source as data.

Also, while the above example is directed to a case where the third aspect and the fourth aspect of the present invention are applied to an automatic printer, the above-described photographic light source spectral energy distribution estimating apparatus may be provided to a photographing apparatus, such as a photographic camera. In this case, the obtained photographic light source spectral energy distribution may be recorded on a film and the spectral energy distribution data recorded on the film may be read in a copying device such as a printer or a visualizing device that effects display on a display.

As described above, a remarkable effect obtained according to the third aspect of the present invention is that it becomes possible to estimate an actual light source by estimating the spectral energy distribution of a light source used in the photography, including a light source whose spectral energy distribution is unknown.

Also, according to the fourth aspect of the present invention, there is provided a practical effect: It becomes possible to realize an exposure amount determining method in which it is possible to determine an exposure amount that is optimal for printing on a duplicating sensitive material, based on the light source energy distribution estimated using the light source energy distribution estimating method according to the third aspect of the present invention.

The light source energy distribution estimating method and apparatus according to the third aspect of the present invention and the exposure amount determining method according to the fourth aspect are basically constructed in the manner described above.

It should be noted here that the embodiments and examples described above are given merely as examples of the present invention. Therefore, the present invention is not limited to these embodiments and examples and it is needless to mention that various modifications and changes may be made as appropriate without departing from the gist of the present invention.

What is claimed is:

1. A light source type discriminating method for discriminating a light source type of a photographic light source, comprising the steps of:
providing first to third sensors respectively having spectral sensitivities corresponding to three primary colors;
arranging a fourth sensor having a spectral sensitivity that does not overlap said spectral sensitivities corresponding to said three primary colors, said first to fourth sensors constituting an image pickup system; and
discriminating said light source type of said photographic light source by using information obtained by said first to fourth sensors, wherein:
said fourth sensor is a sensor in which a value of an average minimum distance $L_{min}$ indicating light source similarity between respective light sources whose types are to be discriminated is at least equal to a predetermined first reference value, said average minimum distance $L_{min}$ being represented by an expression:

$$L_{min} = \Sigma L(i) j_{min}/m \qquad (1)$$

where $L_{min}$ is the average minimum distance, $L(i)j$ is a similarity between a reference light source (i) and another light source (j) and m is a number of types of light sources, and being obtained based on differences between respective sensor signals of said reference light source (i) and respective sensor signals of said another light source (j).

2. The light source type discriminating method according to claim 1, wherein said first reference value is set at 1.2.

3. A light source type discriminating method for discriminating a light source type of a photographic light source, comprising the steps of:
providing first to third sensors respectively having spectral sensitivities corresponding to three primary colors;
arranging a fourth sensor having a spectral sensitivity that does not overlap said spectral sensitivities corresponding to said three primary colors, said first to fourth sensors constituting an image pickup system; and
discriminating said light source type of said photographic light source by using information obtained by said first to fourth sensors, wherein:
said first to third sensors for said three primary colors are respectively a red (R) sensor, a green (G) sensor, and a blue (B) sensor; and
said fourth sensor is a sensor whose absorption peak exists between respective absorption peaks of said G sensor and said B sensor and in a region of from 500 nm to 520 nm.

4. A light source type discriminating method for discriminating a light source type of a photographic light source, comprising the steps of:
providing first to third sensors respectively having spectral sensitivities corresponding to three primary colors;
arranging a fourth sensor having a spectral sensitivity that does not overlap said spectral sensitivities corresponding to said three primary colors, said first to fourth sensors constituting an image pickup system; and
discriminating said light source type of said photographic light source by using information obtained by said first to fourth sensors, wherein said discriminating step comprises:
obtaining a second reference value through one of summation and integration of products of spectral energy distributions of light sources whose color temperatures are each based on known black body radiation, spectral energy distributions of fluorescent lamps whose spectral energy distributions are prescribed, a spectral sensitivity distribution of a photometer system, and a spectral reflectance distribution expressed by a linear combination of predetermined output signal functions of said first to fourth sensors;

measuring as a signal at least a part of reflection light from one of a light source whose color temperature is based on the known black body radiation and a fluorescent lamp whose type is to be discriminated, by using each of said first to fourth sensors;

obtaining a spectral reflectance distribution that minimizes a difference between said second reference value and a measurement value obtained by each of said first to fourth sensors, for each light source whose color temperature is based on said known black body radiation and for each fluorescent lamp;

obtaining as a first evaluation value a sum of abnormal components of the thus obtained spectral reflectance distribution whose maximum values exceed 1.0; and setting, as a result of light source type discrimination, one of a light source whose color temperature is based on said known black body radiation and a fluorescent lamp type corresponding to a minimum value of said first evaluation value.

5. An image forming method for reading image data of an input image with an image pickup system and performing predetermined correction on the read image data, comprising the steps of;

providing first to third sensors respectively having spectral sensitivities corresponding to three primary colors and arranging a fourth sensor having a spectral sensitivity that does not overlap the spectral sensitivities corresponding to the three primary colors, said first to fourth sensors constituting said image pickup system;

discriminating a light source type by using information obtained by said first to fourth sensors;

converting a sensor output obtained with the thus discriminated light source type, by using a color conversion method defined by said sensor output obtained with said discriminated light source type and a sensor output obtained with a desired light source type, so that a sensor output value obtained with said desired light source type is obtained, and obtaining image data of said input image read by said image pickup system using the thus obtained sensor output value; wherein:

said first to third sensors for said three primary colors are respectively a red (R) sensor, a green (G) sensor, and a blue (B) sensor; and when said fourth sensor is assumed to be a sensor X, said fourth sensor X is a sensor whose absorption peak exists between respective absorption peaks of said G sensor and said B sensor and in a region of from 500 nm to 520 nm.

6. An image forming method for reading image data of an input image with an image pickup system and performing predetermined correction on the read image data, comprising the steps of;

providing first to third sensors respectively having spectral sensitivities corresponding to three primary colors and arranging a fourth sensor having a spectral sensitivity that does not overlap the spectral sensitivities corresponding to the three primary colors, said first to fourth sensors constituting said image pickup system;

discriminating a light source type by using information obtained by said first to fourth sensors;

converting a sensor output obtained with the thus discriminated light source type, by using a color conversion method defined by said sensor output obtained with said discriminated light source type and a sensor output obtained with a desired light source type, so that a sensor output value obtained with said desired light source type is obtained, and obtaining image data of said input image read by said image pickup system using the thus obtained sensor output value; wherein:

said first to third sensors for said three primary colors are respectively a red (R) sensor, a green (G) sensor, and a blue (B) sensor; and when said fourth sensor is assumed to be a sensor X, said color conversion method comprises a step of performing correction with respect to a gray portion in said input image or a portion corresponding to the gray portion such that a sensor output $Eij^{ZE}$ (i: pixel position, j: R, G, B, X) corresponding to an estimated light source type becomes a sensor output $Eij^{ZO}$ corresponding to a reference light source.

7. The image forming method according to claim 6, wherein said correction of from said sensor output $Eij^{ZE}$ to said sensor output $Eij^{ZO}$ comprises a step of obtaining coefficient matrices A and C expressed by the following expression:

$$Ei^{ZO} = A \cdot Ei^{ZE} + C \text{ provided that} \quad (11)$$

$$Ei^{ZO} = \begin{vmatrix} EiR^{ZO} \\ EiG^{ZO} \\ EiB^{ZO} \\ EiX^{ZO} \end{vmatrix}, \quad Ei^{ZE} = \begin{vmatrix} EiR^{ZE} \\ EiG^{ZE} \\ EiB^{ZE} \\ EiX^{ZE} \end{vmatrix}$$

where A and C are each a coefficient matrix and C may be zero.

8. The image forming method according to claim 7, wherein said correction of from said sensor output $Eij^{ZE}$ to said sensor output $Eij^{ZO}$ comprises a step of obtaining coefficient matrices A and C expressed by the following expression:

$$\begin{vmatrix} EiR^{ZO} \\ EiG^{ZO} \\ EiB^{ZO} \\ EiX^{ZO} \end{vmatrix} = \begin{vmatrix} AR & 0 & 0 & 0 \\ 0 & AG & 0 & 0 \\ 0 & 0 & AB & 0 \\ 0 & 0 & 0 & AX \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \quad (12)$$

where the coefficient matrix C may be zero.

9. The image forming method according to claim 7, wherein said correction of from said sensor output $Eij^{ZE}$ to said sensor output $Eij^{ZO}$ comprises a step of obtaining coefficient matrices A and C expressed by the following expression:

$$\begin{vmatrix} EiR^{ZO} \\ EiG^{ZO} \\ EiB^{ZO} \\ EiX^{ZO} \end{vmatrix} = \begin{vmatrix} AR_1 & AR_2 & AR_3 & AR_4 \\ AG_1 & AG_2 & AG_3 & AG_4 \\ AB_1 & AB_2 & AB_3 & AB_4 \\ AX_1 & AX_2 & AX_3 & AX_4 \end{vmatrix} \begin{vmatrix} EiR^{ZE} \\ EiG^{ZE} \\ EiB^{ZE} \\ EiX^{ZE} \end{vmatrix} + \begin{vmatrix} CR \\ CG \\ CB \\ CX \end{vmatrix} \quad (13)$$

where the coefficient matrix C may be zero.

10. A light source energy distribution estimating method comprising the steps of;
- obtaining spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions;
- measuring as a signal at least a part of reflection light from a light source whose spectral energy distribution is to be estimated;
- obtaining a spectral reflectance distribution minimizing a difference between said third reference value and a measurement value obtained by said measuring step, for each type of light source energy distribution linear combination;
- obtaining a sum of abnormal components of the thus obtained spectral reflectance distribution whose maximum values exceed 1.0, as a second evaluation value; and
- setting a light source energy distribution linear combination corresponding to a minimum value of said second evaluation value as an energy distribution of said light source whose energy distribution is to be estimated.

11. The light source energy distribution estimating method according to claim 10, wherein said plurality of predetermined functions are each main component vectors obtained from a plurality of pieces of light source data.

12. The light source energy distribution estimating method according to claim 11, wherein as said main component vectors, at least first to third main components of main component vectors obtained from said plurality of pieces of light source data are used.

13. The light source energy distribution estimating method according to claim 10, wherein said third reference value is obtained and stored in a storage unit in advance.

14. A light source energy distribution estimating apparatus comprising:
- storage means for storing spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions;
- measuring means for measuring as a signal at least a part of reflection light from a light source whose spectral energy distribution is to be estimated;
- spectral reflectance distribution calculating means for calculating a spectral reflectance distribution minimizing a difference between said third reference value and a measurement value obtained through measurement with said measuring means, for each type of light source energy distribution linear combination;
- evaluation value calculating means for calculating a sum of abnormal components of the thus obtained spectral reflectance distribution whose maximum values exceed 1.0, as a second evaluation value; and
- estimating means for estimating a light source energy distribution linear combination corresponding to a minimum value of said second evaluation value calculated by said evaluation value calculating means, as an energy distribution of said light source whose energy distribution is to be estimated.

15. The light source energy distribution estimating apparatus according to claim 14, wherein said plurality of predetermined functions are each main component vectors obtained from a plurality of pieces of light source data.

16. The light source energy distribution estimating apparatus according to claim 15, wherein as said main component vectors, at least first to third main components of main component vectors obtained from said plurality of pieces of light source data are used.

17. An exposure amount determining method comprising the step of:
- determining an exposure amount for printing an image onto a duplicating sensitive material so that gray of an image to be printed of a photographic film becomes gray under an estimated light source spectral energy distribution, based on information on said estimated light source spectral energy distribution estimated with a light source energy distribution estimating method and photometric data obtained by photometrically determining at least a part of an image which is photographed on said photographic film under given photographing conditions and whose photographic light source energy distribution is to be estimated,
- wherein said light source energy distribution estimating method comprises the steps of:
- obtaining spectral energy distributions of light sources that are each expressed by a linear combination of a plurality of predetermined functions, a spectral sensitivity of a photometer system, and a third reference value determined by one of summation and integration of products of spectral reflectance distributions that are each expressed by a linear combination of a plurality of predetermined functions;
- measuring as a signal at least a part of reflection light from a light source whose spectral energy distribution is to be estimated;
- obtaining a spectral reflectance distribution minimizing a difference between said third reference value and a measurement value obtained by said measuring step, for each type of light source energy distribution linear combination;
- obtaining a sum of abnormal components of the thus obtained spectral reflectance distribution whose maximum values exceed 1.0, as a second evaluation value; and
- setting a light source energy distribution linear combination corresponding to a minimum value of said second evaluation value as an energy distribution of said light source whose energy distribution is to be estimated.

* * * * *